(12) United States Patent
Raines et al.

(10) Patent No.: US 8,460,684 B2
(45) Date of Patent: Jun. 11, 2013

(54) NUCLEASE INHIBITORS AND METHODS FOR THEIR USE

(75) Inventors: Ronald T. Raines, Madison, WI (US); Bryan D. Smith, Madison, WI (US); Matthew B. Soellner, Madison, WI (US); David M. Lynn, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2136 days.

(21) Appl. No.: 11/084,068

(22) Filed: Mar. 18, 2005

(65) Prior Publication Data
US 2005/0214839 A1 Sep. 29, 2005

Related U.S. Application Data

(60) Provisional application No. 60/554,793, filed on Mar. 19, 2004, provisional application No. 60/635,379, filed on Dec. 10, 2004.

(51) Int. Cl.
*A61F 2/00* (2006.01)

(52) U.S. Cl.
USPC .................. 424/400; 435/6; 435/184; 424/78

(58) Field of Classification Search
USPC ................................ 424/400, 78; 435/6, 184
See application file for complete search history.

(56) References Cited

U.S. PATENT DOCUMENTS

| | | | |
|---|---|---|---|
| 2,348,705 A | 5/1944 | Alderman et al. | |
| 2,515,714 A | 7/1950 | Jones et al. | |
| 5,852,001 A | 12/1998 | Vallee et al. | |
| 5,900,481 A * | 5/1999 | Lough et al. | 506/30 |
| 6,664,379 B1 | 12/2003 | Kudlicki et al. | |
| 7,163,793 B2 | 1/2007 | Kudlicki et al. | |
| 7,264,932 B2 * | 9/2007 | Latham et al. | 435/5 |

FOREIGN PATENT DOCUMENTS

JP 05139981 6/1993

OTHER PUBLICATIONS

Kisilevsky et al Short chain aliphatic polysufonates inhibit the entry of plasmodium into red blood cells, Antimicrobiol agents and chemotherapy, vol. 46, No. 8, pp. 2619-2626, 2002.*
Althaus et al. (1992) "Enzymatic Kinetic Studies with the Non-Nucleoside HIV Reverse Transcriptase Inhibitor U-9843," *Experientia* 48:1127-1132.
Bach, M.K. (1964) "The Inhibition of Deoxyribonucleotidyl Transferase, DNAase and RNAase by Sodium Poly Ethenesulfonic Acid. Effect of the Molecular Weight of the Inhibitor," *Biochim. Biophys. Acta.* 91:619-626.
Breslow et al. (1954) "The Synthesis and Polymerization of Ethylenesulfonic Acid," *J. Am. Chem. Soc.* 76:6399-6401.
Brison et al. (1976) "A Simple and Efficient Method to Remove Ribonuclease Contamination from Pancreatic Deoxyribonuclease Preparations," *Anal. Biochem.* 75:402-409.
Chambon et al. (1967) "Inhibition of RNA Polymerase by Sodium Polyethylene Sulphonate," *Biochim. Biophys. Acta* 149:584-586.
Cheng et al. (1974) "Isolation and Characterization of Modified Globin Messenger Ribonucleic Acid from Erythropoietic Mouse Spleen," *J. Biol. Chem.* 249:1781-1786.
Fellig et al. (1959) "The Inhibition of Pancreatic Ribonuclease by Anionic Polymers," *Arch Biochim. Biophys.* 85:313-316.
Heymann et al. (1958) "The Inhibition of Ribonuclease by Acidic Polymers and Their Use as Possible Antiviral Agents," *Arch. Biochem. Biophys.* 73:366-383.
Jones, G.H. (1976) "On the Efficacy of Commonly Used Ribonuclease Inhibitors," *Biochim. Biophys. Res. Commun.* 69:469-474.
Kisilevsky et al. (2002) "Short-Chain Aliphatic Polysulfonates Inhibit the Entry of *Plasmodium* into Red Blood Cells," *Antimicrob. Agents. Chemother.* 46(8):2619-2626.
Littauer et al. (1962) "An Ultracenterfugal Study of the Efficiency of Some Macromolecular Inhibitors of Ribonuclease," *Biochim. Biophys. Acta.* 61:609-611.
Mach et al. (1968) "Chemical Identification of Specific Immunoglobulins as the product of a call-free System from Plasmocytoma," *Proc. Natl. Acad. Sci. USA* 59:445-452.
Narang et al. (1995) "Removal of Ribonucleases from Solution Using an Inhibitor-Based Sol-Gel-Derived Biogel," *Anal. Chem.* 67:1935-1939.
Rahman et al. (1996) "Selective Removal of Ribonucleases from Solution with Covalently Anchored Macromolecular Inhibitor," *Anal. Chem.* 68:134-138.
Richards et al. (1971) *The Enzymes*, Boyer, P.D. eds., vol. IV, $3^{rd}$ Ed., Academic Press, New York, pp. 647-806.
Smith et al. (2003) "Potent Inhibition of Ribonuclease A by Oligo(vinylsulfonic Acid)," *J. Biol. Chem.* 278(23):20934-20938.
Smith et al. (Dec. 2005) "Synthetic Surfaces for Ribonuclease Adsorption," *Langmuir* 21(1):187-190.
Tunis et al. (1963) "A Comparative Study of the Inhibiting Effects of Anionic Polyelectrlytes on Deoxyribonucleases," *Biochem. Biophys.* 101:448-455.
Wang, D.; Moore, S. (1978) "Preparation of protease-free and ribonuclease-free pancreatic deoxyribonuclease," *J. Biol. Chem.* 253:7216-7219.
Wilchek, M.; Gorecki, M. (1969) "Affinity Chromatography of Bovine Pancreatic Ribonuclease A," *Eur. J. Biochem.* 11:491-494.
Niehaus et al. (1993) "A Potent Specific Inhibitor of 6-Phosphogluconate Dehydroginase of Cryptococcus Neoforms and of Certain Other Fungal Enzymes," Mycopathologia 123:155-158.
Niehaus et al. (Dec. 1995) "Polyethylene Sulfonate: A Tight-Binding Inhibitor of 6-Phosphogluconate Dehydrogenase of Cryptococcus Neoformans," Arch. Biochem. Biophys. 324:325-330.
Park et al. (2000) "Origin of the 'Inactivation' of Ribonuclease A at Low Salt Concentration," FEBS Lett. 468:199-202.

* cited by examiner

*Primary Examiner* — Brandon Fetterolf
*Assistant Examiner* — Jean Cornet
(74) *Attorney, Agent, or Firm* — Lathrop & Gage LLP

(57) ABSTRACT

A class of anionic oligomers and polymers that function for inhibition of nucleases, particularly RNase. Specific inhibitors include mixtures of oligomers of vinyl sulfate. Methods for inhibition or inactivation of one or more nucleases in vitro which comprises the step of contacting the one or more nucleases in a biological medium with one or more of the anionic oligomeric or polymeric inhibitors of this invention. Kits for carrying out a biological procedure, biological reaction and/or a biological assay containing one or more inhibitors of this invention. The use of oligomers and/or polymers of this invention as additives in buffers or reagents. The inhibitors of the invention can also be attached to surfaces to provide for removal of nucleases from media, solutions or other liquids in contact with the solid.

33 Claims, 9 Drawing Sheets

ACES

BES

CHES

HEPES

MES

PIPES

NUCLEASE INHIBITORS AND METHODS FOR THEIR USE

CROSS-REFERENCE TO RELATED APPLICATIONS

This application claims the benefit under 35 U.S.C. 119(e) to U.S. patent application No. 60/554,793, filed Mar. 19, 2004, and to U.S. patent application No. 60/635,379, filed Dec. 10 2004, both of which are incorporated by reference in their entirety herein.

STATEMENT REGARDING FEDERALLY SPONSORED RESEARCH OR DEVELOPMENT

This invention was made with government support under GM044783 awarded by the National Institutes of Health. The government has certain rights in this invention.

BACKGROUND OF THE INVENTION

This invention relates to the identification of a class of nuclease inhibitors, e.g., ribonulcease (RNase) inhibitors. The inhibitors bind to and inhibit nucleases, particularly RNases. The invention provides methods for removing these inhibitors from buffers and other reagents employed in research to generate purified buffers and reagents useful for applications involving RNase and other nucleases. The invention further provides methods for inhibiting RNase and other nucleases using one or more of the inhibitors identified. The invention also relates to methods and materials for removing undesired RNase and other nucleases from biological media.

Biochemical research and biotechnology rely on polymeric nucleic acids. Yet during their storage and use, nucleic acids encounter nucleases, both advertently and inadvertently. For example, nucleases are often added with the intent of destroying RNA in a DNA sample, or vice versa. Residual amounts of these nucleases can affect downstream steps in protocols. (Pasloske, B. L. In Nuclease Methods and Protocols, Schein, C. H., Ed. Humana Press: Totowa, N.J., 2001; pp 105-111; Sweeney, R. Y.; Kelemen, B. R.; Woycechowsky, K. J.; Raines, R. T. Anal. Biochem. 2000, 286, (2), 312-314). Alternatively, human skin is an abundant source of nucleases that can be transferred accidentally to surfaces and solutions (Holley, R. W.; Apgar, J.; Merrill, S. H. J. Biol. Chem. 1961, 236, PC42-43.) Moreover, reagents (including those labeled "nuclease free") are often contaminated with nucleases (Hengen, P. N. Trends Biochem. Sci. 1996, 21, (3), 112-113).

RNA is the least stable of the biopolymers that effect information transfer in biology (Wolfenden, R., and Snider, M. J. (2001) Acc. Chem. Res. 34, 938-945). The lifetime of RNA in vivo is most often determined by measuring the rate of its enzymatic degradation (Ross, J. (1996) Trends Genet. 12, 171-175). Ribonucleases are perhaps the most problematic of nucleases because of their high natural abundance, prodigious catalytic activity, notorious conformational stability and resistance to proteolysis, and lack of requisite cofactors. (D'Alessio, G.; Riordan, J. F., Ed., Ribonucleases: Structures and Functions. Academic Press: New York, 1997; Raines, R. T. Chem. Rev. 1998, 98, 1045-1065).

In vitro, ribonuclease inhibitors are often employed to mitigate damage to RNA from incidental (or inadvertent) contamination with secretory ribonucleases such as the human homolog of ribonuclease A (RNase A, 1 EC 3.1.27.5) (Raines, R. T. (1998) supra). The abundance and diversity of natural ribonucleases has led to an ever-increasing interest in inhibitor design and discovery (Russo, A., Acharya, K. R., and Shapiro, R. (2001) Methods Enzymol. 341, 629-648). Although several ribonuclease inhibitors have been described, each suffers from one or more undesirable attribute (See: Pasloske (2001) supra; Raines (1998) supra; Russo, A.; Acharya, K. R.; Shapiro, R. Methods Enzymol. 2001, 341, 629-648.) For example, the ribonuclease inhibitor protein (RI) binds ribonucleases with femtomolar affinity (Hofsteenge, J. In Ribonucleases: Structures and Functions, D'Alessio, G.; Riordan, J. F., Ed. Academic Press: New York, 1997; pp 621-658; Shapiro, R. Methods Enzymol 2001, 341, 611-628), but is expensive and highly sensitive to oxidation (Kim, B.-M.; Schultz, L. W.; Raines, R. T. Protein Sci. 1999, 8, 430-434). In addition, RI inhibits only ribonuclease A (RNase A6, 11; EC 3.1.27.5) and some of its homologs. Although diethylpyrocarbonate (DEPC) inactivates many nucleases, it is toxic and its use requires time-consuming procedures. Moreover, DEPC-treatment results in the covalent modification of many proteins, nucleic acids, and small molecules (Miles, E. W. Methods Enzymol. 1977, 47, 431-442).

In vitro, ribonuclease inhibitors are useful in a variety of molecular biology applications where RNase contamination is a potential problem. Examples of these applications include RNA isolation, purification and storage, particularly mRNA isolation and purification, assays characterizing or employing RNA, reverse transcription of mRNA, cell-free translation systems, preparation of RNase-free antibodies, reverse transcription-PCR and in vitro virus replication.

Ideally, ribonuclease inhibitors to be used in these kinds of applications will be capable of inhibiting a large number of different RNases, such as eukaryotic RNase A, RNase B and RNase C, as well as prokaryotic RNases. Thus, there is a need in the art for ribonuclease inhibitors for various applications.

We have recently reported that MES-NaOH buffer (pH 6.0) inhibits catalysis by RNase A and a variant thereof designated K7A/R10A/K66A at low salt concentrations (Park and Raines (2000) FEBS Lett. 468, 199-202). The inhibitor was described in this reference as "highly charged," anionic and not polymeric. The origin of RNase inhibition in the buffer was described as "low levels of small anions in common buffer solution." The K7A/R10A/K66A RNase A variant has three fewer cationic residues than does the wild-type enzyme [Fisher, B. M., Ha, J.-H. and Raines, R. T. (1998) Biochemistry 37, 12121-12132; Fisher, B. M., Schultz, L. W. and Raines, R. T. (1998) Biochemistry 37, 17386-17401] and is effectively missing two of the four known subsites for phosphoryl group binding [Fisher, B. M., Grilley, J. E. and Raines, R. T. (1998) J. Biol. Chem. 273, 34134-34138; Nogues, M. V., Moussaoui, M., Boix, E., Vilanova, M., Ribo, M. and Cuchillo, C. M. (1998) Cell. Mol. Life Sci. 54, 766-774].

This invention is based at least in part on the identification of the inhibitor(s) in MES-NaOH (2-(N-morpholino)ethane sulfonate-NaOH) buffer as relatively low molecular weight oligomers of vinyl sulfonic acid, e.g.:

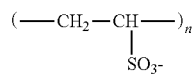

where n represents the number of monomers. Smith et al. (2003) J. Biol. Chem., which is incorporated by reference herein to the extent that it is not inconsistent with the disclosure herein, provides details of the identification of the inhibitors.

Various low molecular weight RNase inhibitors, including nucleosides and nucleotides, have been identified (Richards and Wyckoff, 1971; Sambrook, J. et al. (1982) "Molecular Cloning, A Laboratory Manual" Cold Spring Harbor Laboratory and later editions). Uridine-vanadate (UV) is a particularly potent RNase inhibitor with Ki=10 µM at pH 7 (Linquist, R. N. et al. (1973) J. Amer. Chem. Soc. 95:8762-8768; Wlodawer, A. et al. (1983) Proc. Natl. Acad. Sci. USA 80:3628-3631.)

Ribonucleoside vanadyl complex mixture is a commercial product (Sigma-Aldrich, described as inhibiting approximately $2 \times 10^4$ Kunitz units/ml of RNase A at 20 mM) used as a ribonuclease inhibitor during cell lysis and mRNA purification (Berger, S. L. and Birkenmeier, C. S. (1979) Biochemistry 18:5145.). U.S. Pat. No. 5,852,001 reports RNase inhibitors that are nucleotides having diphosphate groups.

Additional reported ribonulcease inhibitors include certain clays (e.g., bentonite and macaloid), certain surfactants (e.g., SDS, EDTA); proteinase K and ammonium sulfate (see: Jocoli and Ronald (1973) Can. J. Biochem, 51:1558-1565; Jones (1976) Biochem Biophys Res. Commun, 69:469-474; Mendelsohn and Young Biochem. Biophys. Acta (1978) 519: 461-473; Allewell and Sama (1974) Biochem. Biophys. Acta, 341-484-488.).

The 50-kD ribonuclease inhibitor protein (RI) forms a tight 1:1 complex with RNase A (Kd~$10^{-14}$) (Lee et al., 1989) chelating all of its phosphoryl group binding subsites (Kobe and Deisenhofer, 1996.) The utility of pyrophosphate linked oligonucleotides and ribonuclease inhibitor is limited, both by the difficulty and expense of their production and by their intrinsic instability (Russo and Shapiro, 1999; Kim, et al., 1999)

U.S. Pat. No. 6,664,379 reports methods and compositions for inhibiting nucleases using anti-nuclease antibodies.

Certain polyanions are reported to be effective inhibitors of RNase A (Richards and Wyckoff, 1971). Heparin, tyrosineglutamate copolymers, and a number of different polysulfates and polyphosphates are reported to inhibit catalysis by the enzyme (Sela, 1962; Zollner and Fellig, 1953; Heymann et al., 1958).

Poly(vinylsulfonic acid) (or poly(vinyl sulfonate) (PVS), also called polyethenesulfonic acid, PES) is reported to inhibit RNase activity at pH 7.6 (M. K Bach, 1964). PVS samples having molecular weight ranging from 5,700 (g/mol) to 27,600 (g/mol) were assessed for inhibition of RNase at various concentrations. Molecular weights were reported to be estimated by a combination of light scattering, viscosimetric analysis and ultracentrifugation essentially as in Dailer and Kerber (1955) Makromol. Chem. 17:56. Percent inhibition of RNase was reported to generally increase with increasing molecular weight of the PVS and increasing amount of the PVS present. The results presented for the lowest molecular weight PVS assessed do not exhibit consistent inhibition. PVS of molecular weight 5,700 exhibited inhibition at an intermediate concentration, but not at lower or higher concentrations. PVS of molecular weight 6400 exhibited stimulation of RNase at lower concentrations and inhibition of RNase at the higher concentration tested. Results reported for inhibition of RNase by PVS of molecular weight 12,900 also appear inconsistent with the general trend of the data presented. The reference suggests that only longer polymers with molecular weight greater than 9,000 were good inhibitors of RNase.

PVS is also reported to be a potent inhibitor of DNase (Tunis M. and Regelson W. Arch. Biochem. Biophys. 1963 101, 448-455; Bach (1964) supra).

Fellig and Wiley, 1959 reported that polyvinyl sulfonate was a "fairly effective" inhibitor of ribonuclease (pancreatic) compared to sulfated polyvinyl alcohol which was described as "a very strong inhibitor." Inhibition by polyvinyl sulfonate was reported to decrease markedly with increasing sodium chloride concentration. The molecular weight of the polyvinyl sulfonate employed in these experiments was not reported.

In contrast, Littauer and Sela, 1962 reported that PVS (having reported molecular weight of 300,000) exhibited no significant activity on crude ribosomal E. Coli RNase at pH 7.4.

Cheng et al., 1974 report that their isolation of spleen mRNA was carried out in the presence of an RNase inhibitor, such as polyvinylsulfate or bentonite. The molecular weight and source of the polyvinylsulfate used was not reported. Mach et al., 1968 employed polyvinyl sulfonic acid in a cell-free system for active protein synthesis. The reference, however, does not report the function of the polyvinylsulfonic acid used and the source and molecular weight of the material is not given.

Niehaus W. G. and Flynn T. (1993) Mycopathologia 123 (3): 155-158 reported that a contaminant of MES buffer inhibited a number of fungal NADP-dependent dehydrogenases. The inhibitor was identified as an "ethylenesulfonic acid oligomer" and it was suggested to be a "model compound" for the development of an antifungal agent. It was reported that the MES buffer contained large polymers (~50,000 g/mol) of ethylenesulfonic acid (i.e., polyvinyl sulfonate.) In a later publication, Niehaus W. G. et al. (1995) Arch. Biochem. Biophys. 324(2):325-330), it was reported that polyvinyl sulfonate (Mr (relative molecular weight)= 50,000) was a potent inhibitor of a number of fungal enzymes.

Japanese published patent application 05139981 A (published Jun. 8, 1993) Abstract (Eng) reports that the sodium salt of vinylsulfonic acid polymer (PVS), as well as several other sulfonated polymers, function as antiviral agents, particularly against HIV. These agents are described as having "inhibitory activity for cytoclasis due to human immunodeficiency virus, inhibitory activity for giant cell formation and anti-human immunodeficiency virus activity such as reverse transcriptase inhibitory activity."

R. Kisilevsky et al., 2002 reports that short-chain aliphatic polysulfonates inhibit the entry of Pasmodium into red blood cells and may be useful as antimalarial agents. Two samples of poly(vinylsulfonate sodium salt) were employed which were "mixtures of oligomeric species with slightly different chain lengths and stereochemistry." The first (designated compound 1) was prepared from commercial poly(vinylsulfonate sodium salt) (Aldrich Company, catalog no. 27,842-4, a 25% (wt/wt) solution in water) as follows:

(The) solution (2 liters) was concentrated under reduced pressure to half of its volume. Ethanol (200 ml) was added, followed by the addition of activated carbon (50 g). The mixture was warmed on a steam bath for 20 min and then filtered through Celite, and the solvent was removed under reduced pressure to give a light-yellowish oil. The oil was dried in a vacuum oven (50° C.) for 3 days to give an amorphous solid (486 g).

The molecular weight distribution was determined using gel permeation chromatography by a commercial laboratory (American Polymer Standards) and reported as follows: number-average molecular weight (Mn)=1,800; weight-molecular weight (Mw)=3,050; z-average molecular weight (Mz)=5, 400; Mw/Mn (polydispersity index)=1.69.

The second sample of poly(vinylsulfonate sodium salt) (designated compound 2) was prepared by radical polymerization of sodium vinylsulfonate in the presence of sodium persulfate. Commercially available sodium vinylsulfonate (Aldrich, catalog no. 27,841-6) as a 25% (wt/wt) solution in water was employed. The sodium vinylsulfonate solution was diluted in water 160 ml of the 25% (wt/wt) solution in (160 ml water) and purged with argon for 30 min. A solution of sodium persulfate (1.6 g) in $H_2O$ (30 ml) was similarly purged. The purged solutions were mixed and the mixture was heated (under argon) at 80° C. in an oil bath for 17 h. The reaction mixture was concentrated under reduced pressure to 100 ml; addition of methanol (1 liter) gave a white solid which was dried in a vacuum oven (75° C.) overnight to give compound 2. The molecular weight distribution of compound 2 as determined by gel permeation chromatography (American Polymer Standards Corporation) was reported as follows: Mn=1,600; Mw=2,000; Mz=2,700; and Mw/Mn=1.25.

Compound 1 is reported to have an $IC_{50}$ of 0.2 µM (on the basis of the weight molecular weight of 3,050) for *Plasmodium falciparum* viability in human red blood cells. Compound 2 is reported to have an IC 50 of 6±2 µM (on the basis of a weight molecular weight of 2,000) in the same assay. The poly vinylsulfonate sample (compound 1) having higher weight molecular weight was found to be more effective against *P. Falciparum*. Aliphatic polysulfonates were said to be potent inhibitors of merozoite invasion of red blood cells and to possibly constitute a novel class of antimalarials. It is suggested that compounds 1 and 2, of the reference, are inhibiting the initial step of the invasion process, possibly by interacting with a merozite surface protein or with a red blood cell receptor.

Kisilevsky et al. (1995) Nature Medicine 1(2):143-148 reports experiments on arresting amyloidosis in vivo using small-molecule anionic sulfonates and sulfates. Poly (vinylsulfonate sodium salt) as a 25% (wt/wt) solution (Aldrich, 27, 842-4) "processed to provide an amorphous solid" said to have a molecular weight distribution of 900-1,000 was reported to interfere with heparin sulfate-stimulated β-peptide fibril aggregation in vitro and to substantially reduce murine splenic AA amyloid progression in vivo. The method by which PVS samples were processed prior to use was not provided.

SUMMARY OF THE INVENTION

This invention provides a class of anionic oligomers and polymers that function for inhibition of nucleases, particularly RNase. In specific embodiments the inhibitors are anionic oligomers, polymers or both and mixtures thereof of formula:

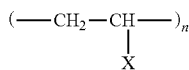

where X is $-SO_3^-$, $-OSO_3^-$, $-PO_3H^-$, or $-OPO_3H^-$ and n is an integer representing the number of repeating monomer units and n is 8 or more. In specific embodiments, the inhibitor is a mixture of oligomers of vinyl sulfonate in which n ranges from about 8 to about 20. In other specific embodiments, the inhibitor is a mixture of oligomers of vinyl sulfate or mixtures of oligomers of vinyl phosphonate in which n ranges from about 8 to about 20. In other specific embodiments, the anionic oligomers, polymers or both are immobilized on a solid support.

The invention provides a method for inhibition or inactivation of one or more nucleases, particularly RNases, in vitro which comprises the step of contacting the one or more nucleases in a biological medium with one or more of the anionic oligomers, polymers or both and mixtures thereof of formula:

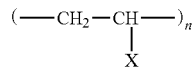

where X is $-SO_3^-$, $-OSO_3^-$, $-PO_3H^-$, or $-OPO_3H^-$ and n is an integer representing the number of repeating monomer units and n is 8 or more. The one or more anionic oligomers, polymers or both are present in contact with one or more nucleases in an amount sufficient to inhibit at least one of the one or more nucleases present. Typically, the inhibitor is employed in a biological medium in which a nuclease, particularly a ribonuclease, is a component in the biological medium. Preferably, the inhibitor is added in an amount sufficient to prevent breakdown of any nuclease, particularly any ribonuclease, present. In a more specific preferred embodiment, the inhibitor is employed to inhibit RNase and is provided in an amount in excess of its Ki for RNase and more preferably in a 10-100 excess (molar or by weight) over its Ki for RNase. In specific embodiments, the inhibitor is a mixture of oligomers of vinyl sulfonate in which n ranges from about 8 to about 20. In other specific embodiments, the inhibitor is a mixture of oligomers of vinyl sulfate or mixtures of oligomers of vinyl phosphonate in which n ranges from about 8 to about 20.

The invention further provides kits for carrying out a biological procedure, biological reaction and/or a biological assay in which it is desirable or necessary to inhibit one or more nucleases, particularly RNases. The kits of the invention comprise one or more of the anionic oligomers, polymers or both and mixtures thereof of the above formula. The kits of the invention can include one or more than one separately packaged, pre-weighed or pre-selected volumes, of inhibitors of this invention. Pre-selected amounts of inhibitors of this invention may also be present in buffer and or reagent components in kits for carrying out procedures, reactions or assays. Inhibitors in such kits can be provided immobilized on a solid support. Kits may include other reagents, buffers and the like for carrying out the procedure, reagent and/or assay for which the inhibitor is intended. The kit may further contain instructions for employing the inhibitor and/or carrying out the procedure, reagent and/or assay. Specific kits include, among others, those for carrying out m-RNA isolation and/or purification, those for carrying out an in vitro transcription and/or translation, those for carrying out RT-PCR; those for carrying out any RNA diagnostic.

The oligomers and/or polymers of this invention can also be employed to as additives in buffers or reagents that are specifically intended for use in reactions, procedures or assays which would be detrimentally affect by the presence of nucleases, particularly RNases.

The invention also provides oligomers and or polymers of this invention which are covalently attached to a solid support or a surface. More specifically, surface-or solid-bound inhibitors of this invention include those of formula:

where X is $-SO_3^-$, $-OSO_3^-$, $-PO_3H^-$, or $-OPO_3H^-$, m can, in general, range from about 8 to 1,500, or more, L is a linker or spacer group and S is a solid particle or surface. In specific embodiments, the solid is silica gel or glass. In specific embodiments, S is a solid particle or bead. In other specific embodiments, S is a surface, e.g., a glass surface. In more specific embodiments, the surface that carries the oligomer and/or polymer is the internal surface of a container in which a buffer or reagent is to be carried or stored or in which a procedure, purification, isolation, assay or reaction is to be carried out. The internal surface of the container is provided with an amount of bound oligomer and/or polymer sufficient to bind to nucleases that may be present.

The invention also provides a method for removing nucleases, particularly RNases from biological medium, including, among others, buffers, reagents, reaction medium, assay medium, and RNA storage medium. The method comprises the step of adding a solid carrying covalently linked oligomer and/or polymer of this invention to the biological medium. The solid is kept in contact with the biological medium for a sufficient time to bind nuclease that may be in the medium to the oligomers and/or polymers on the solid. The solid can optionally be removed after this time to remove nucleases from the biological medium. Alternatively, the solid can be retained in contact with the biological medium to continue to bind to any nucleases that may thereafter be inadvertently (or intentionally) added to the medium.

Solid particles carrying the oligomers and/or polymers of this invention can also be used to inhibit and/or inactivate nucleases, particularly RNases in biological medium.

More generally the solid particles and surfaces carrying oligomers and/or polymers of this invention can be employed to bind to any RNA-binding protein or fragment there of or to any DNA-binding protein or fragment thereof. These solids and surfaces can be employed to remove RNA-binding proteins or DNA-binding proteins from biological media. These solids and surfaces can be employed to isolate RNA-binding proteins or DNA-binding proteins from biological media. In a specific embodiment, the solids and surfaces carrying the oligomers and/or polymers of this invention can be employed to isolate RNA-binding and/or DNA binding proteins and peptides from mixtures of proteins and/or peptides, and particularly from combinatorial libraries of proteins and/or peptides.

In specific embodiments the invention provides, solid surfaces coated with poly(vinylsulfonate), particularly those surfaces which are silica gel surfaces or glass surfaces. The invention provides silica gel carrying immobilized poly(vinylsulfonate) and glass elements carrying surface-immobilized poly(vinylsulfonate). Glass elements carrying immobilized poly(vinylsulfonate) can be any size or shape and include among others, glass slides, glass plates, and glass beads. Further, glass elements may be glass bottles or other containers wherein at least a portion of the inside surface of the container carries surface-immobilized poly(vinylsulfonate).

In specific embodiments, the invention provides a method for removing nucleases from a solution that may contain nucleases which comprises the step of contacting the solution with a solid surface to which poly(vinyl sulfonate) is immobilized. Immobilization is preferably accomplished by covalent attachment of poly(vinyl sulfonate), optionally via a linker group, to the surface. In another specific embodiment, the invention provides a method for preventing degradation of nucleic acids by nucleases in a solution that may contain one or more nucleases or which may become contaminated with one or more nucleases which comprises the step of contacting the solution with a solid surface to which poly(vinylsulfonate) is immobilized.

The invention further relates to procedures, reactions, assays, and purifications carried out in the presence of an inhibitory amount of one or more oligomers and/or polymers of this invention. The oligomers and/or polymers of this invention can be added to a biological medium that is not known to contain nuclease as a precaution against the detrimental effects of the presence of nucleases.

The present invention is based at least in part on the identification and successful removal of low molecular weight RNase inhibitors present in commercial ethanesulfonate buffers. The inhibitors were identified as oligomers of vinyl sulfonate. The invention, thus, also provides a method for removing RNase inhibitors from ethanesulfonate buffers (i.e., any buffer which comprises ethane sulfonate) which method comprises the step of contacting the buffer with an anion exchange resin for a sufficient time to remove the oligomers. The method is particularly useful for removing RNase inhibitors from MES buffers (i.e., any buffer which comprises 2-(N-morpholino)ethane sulfonate. Preferably the anion exchange resin is a strong base anion exchange resin. The method optional comprises a step of assaying the buffer after contact with the anion exchange resin to verify that the inhibitory oligomers have been removed. If inhibitory oligomers remain, the step of contacting with the anion exchange resin can be repeated, until a desired low level of RNase inhibition remains. RNase inhibition can be measured by any art-known method. The invention provides ethane sulfonic acid buffers which contain reduced levels of RNase inhibitors. The invention further provides ethanesulfonate buffers which contain no detectible level of the oligomeric RNase inhibitor. Oligomers of vinyl sulfonate can be detected, for example, by mass spectrometric analysis or other methods that are known in the art.

Further embodiments of the invention will be evident from consideration of the following detailed description.

BRIEF DESCRIPTION OF THE DRAWINGS

In FIG. 4A, assays were performed at 25° C. in 50 mM imidazole-HCl buffer, pH 6.0, containing NaCl (■, 0M; ●, 0.05M; ▲, 0.10M; and ◆, 0.25M). Rates determined at 0.05-0.25 M NaCl were fitted to Equation 1 (see text.) Rates determined at 0 M NaCl were fitted to Equation 2 (see text.)

In FIG. 4B, values of Ki were calculated from the data in FIG. 4A. [Cation] refers to the concentration of Na+ plus imidazolium ion.

FIG. 6A is a Scatchard plot for the adsorption of RNase A by PVS-coated silica in 50 mM MES-NaOH buffer, pH 6.0, containing NaCl (0.10 M). Data are for tight-binding sites; FIG. 6B is a graph of RNase activity in the presence of immobilized PVS and FIG. 6C is a graph of RNase activity in the presence of a control acrylamide resin.

DETAILED DESCRIPTION OF THE INVENTION

Figure 1:
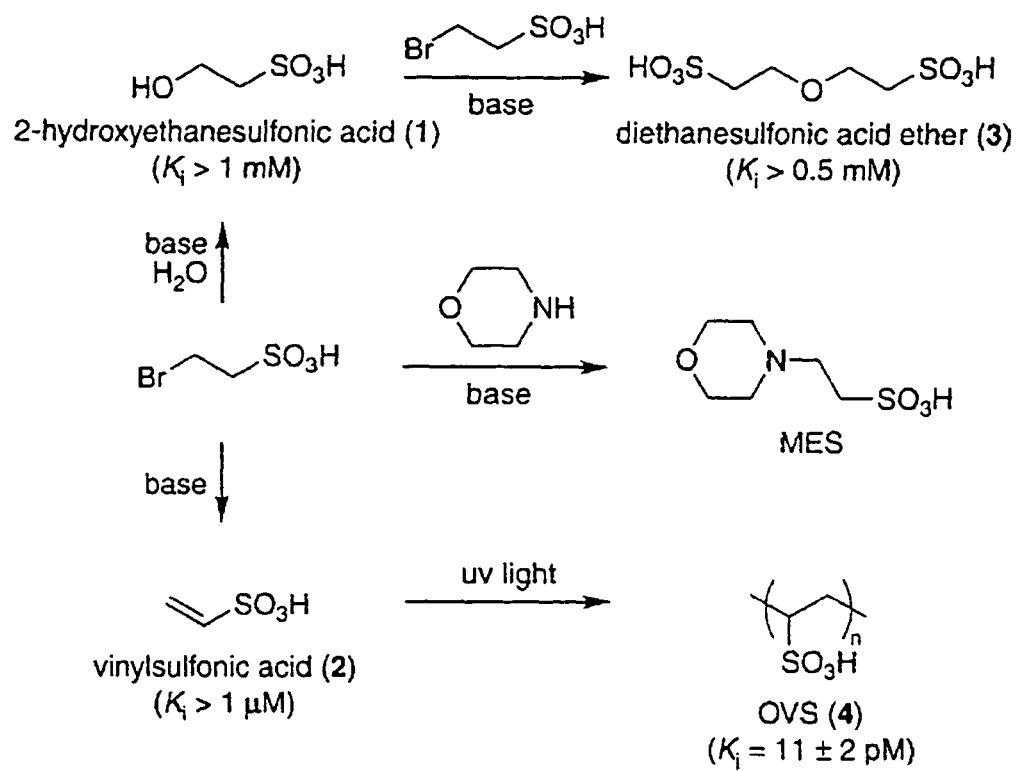
FIG. 1 illustrates byproducts of MES buffer synthesis. Values of Ki are listed for inhibition of catalysis of 6-FAM~dArUdAdA~6-TAMRA cleavage by ribonuclease A in 50 mM imidazole-HCl buffer, pH 6.0. The Ki for OVS inhibition is calculated based on a molecular mass of 2,000 g/mol (Mn value reported by commercial source, Polysciences).

The present invention relates to methods for inhibiting and/or inactivating nucleases or for removing nucleases from biological media. Nucleases are inhibited or inactivated by contact with water-soluble anionic oligomers and/or polymers.

More specifically the oligomeric and/or polymeric anions are those having the formula:

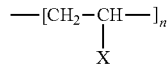

where X is $-SO_3^-$, $-OSO_3^-$, $-PO_3H^-$, or $-OPO_3H^-$ and n can, in general, range from about 8 to 1,500 or more. The anionic oligomers and/or polymers may be provided as the corresponding acids or as salts, e.g., alkali metal salts. More specifically, inhibitory oligomers have n from about 8 to about 25. Preferred oligomers have n from 9 to about 17, and more preferred oligomers have n from 9 to 13. Inhibitory oligomers include those in which X is $-SO_3^-$ and n is about 8 to about 25, those in which X is $-SO_3^-$ and n is about 9 to about 17 and those in which X is $-SO_3^-$ and n is 9-13. Inhibitory polymers are those of the above formula where n is more than 25. In specific embodiments, inhibitory polymers include those of the above formula where n is greater than 25 and less than or equal to about 1,000. More specifically, inhibitory polymers include those in which X is $-OSO_3^-$, or $-PO_3H^-$ or $-OPO_3H^-$ and n is greater than 25. Inhibitory polymers include those in which n is greater than 25 and less than or equal to about 500. Inhibitory polymers include those in which n is greater than 25 and less than or equal to about 100. Inhibitory polymers include those in which n is greater than 25 and less than or equal to about 50. Inhibitory polymers include those in which X is $-OSO_3^-$, $-PO_3H^-$, or $-OPO_3H^-$ and n is greater than 25 and less than or equal to about 500. Inhibitory polymers include those in which X is $-OSO_3^-$, $-PO_3H^-$, or $-OPO_3H^-$ and n is greater than 25 and less than or equal to about 100. Inhibitory polymers include those in which X is $-OSO_3^-$, $-PO_3H^-$, or $-OPO_3H^-$ and n is greater than 25 and less than or equal to about 50.

The invention provides nuclease inhibitory compositions which comprise one or more of the oligomers and/or polymers of the above formula present in the composition in an inhibitory amount and a biologically acceptable carrier, which may be a biological medium. Typically, the inhibitory compositions comprise a mixture of more than one oligomer and/or polymer of the above formula. Inhibitory compositions include those in which 50% or more of the inhibitory activity of the composition is attributable to the oligomers therein. Inhibitory compositions include those in which 90% or more of the inhibitory activity of the composition is attributable to the oligomers therein. Inhibitory compositions include those wherein no detectable level of polymer (with n over 25) is present. Inhibitory compositions include those in which X is $-SO_3^-$ and in which 50% or more of the inhibitory activity of the composition is attributable to the oligomers therein. Inhibitory compositions include those in which X is $-SO_3^-$ and in which 90% or more of the inhibitory activity of the composition is attributable to the oligomers therein. Inhibitory compositions include those in which X is $-O-SO_3^-$ and wherein no detectable level of polyvinylsulfonate (n over 25) is present. Inhibitory compositions include those in which X is $-O-SO_3^-$ and in which 50% or more of the inhibitory activity of the composition is attributable to the oligomers therein. Inhibitory compositions include those in which X is $-O-SO_3^-$ and in which 90% or more of the inhibitory activity of the composition is attributable to the oligomers therein. Inhibitory compositions include those in which X is $-O-SO_3^-$ and wherein no detectable level of polyvinylsulfate (n over 25) is present.

Mixtures of oligomers and/or polymers of this invention can be characterized by average molecular weight measurements. For example, mixtures of oligomers and/or polymers can be characterized by any one or more of number-average molecular weight (Mn); weight-average molecular weight (Mw); z-average molecular weight (Mz); and/or Mw/Mn (polydispersity index). These values can be obtained for mixture of oligomers and/or polymers using experimental methods (light scattering methods, viscosity measurements, etc.) as are known in the art. All of these values can be obtained from the molecular weight distribution which can be determined, for, example by gel permeation chromatography or mass spectrometry as is known in the art. Such measurements can be performed by commercial vendors such as American Polymer Standards.

In specific embodiments, the inhibitory oligomers and/or polymers herein have Mn, Mw, and/or Mz of less than about 100,000. In specific embodiments, the inhibitory oligomers and/or polymers herein have Mn, Mw, and/or Mz less than about 50,000. In specific embodiments, the inhibitory oligomers and/or polymers herein have Mn, Mw, and/or Mz of less than about 10,000. In specific embodiments, the inhibitory oligomers and/or polymers herein have Mn, Mw, and/or Mz of less than about 5,000. In specific embodiments, the inhibitory oligomers and/or polymers herein have all of Mn, Mw, and Mz less than about 5,000. In specific embodiments, the inhibitory oligomers and/or polymers herein have Mn, Mw and Mz less than about 2,000. In specific embodiments, the inhibitory oligomers and/or polymers herein have Mn less than about 2,000 or less than about 1,000.

In specific embodiments, the inhibitory oligomers and/or polymers herein wherein X is —$SO_3^-$ have Mn, Mw, and/or Mz of 5,000 or less, Mn of less than about 2,000 or less than about 1,000. In specific embodiments, the inhibitory oligomers and/or polymers herein have all of Mn, Mw, and Mz less than 5,000. In specific embodiments, the inhibitory oligomers and/or polymers herein have Mn of about 2,000 or less. In specific embodiments, the inhibitory oligomers and/or polymers herein have Mw between about 4,000 and 6,000.

Nucleases are inhibited and/or inactivated or are removed from biological media employing covalently immobilized anionic oligomers and/or polymers of formula:

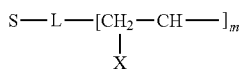

where X is —$SO_3^-$, —$OSO_3^-$, —$PO_3H^-$, or —$OPO_3H^-$, m can, in general, range from about 8 to 1,500, or more, L is a linker or spacer group and S is a solid. The covalently immobilized oligomers and/or polymers of this formula bind to one or more nucleases to thereby inhibit or inactivate nuclease function. The solid to which the oligomer and/or polymer is bound and to which one or more nucleases in turn binds, can be removed from a biological medium, thereby removing the nucleases. The solid is any solid particle or surface that is compatible with the biological medium and to which a covalent bond can be made. Solids in the form of beads or similar particles can be filtered or otherwise separated from the biological medium. Particles may be irregularly shaped or regular in shape, e.g., spherical. In a specific embodiment, the solid is a glass or plastic surface in contact with the biological medium which may contain one or more nucleases, for example, the solid is an internal surface of a container for receiving a biological medium.

Surfaces or solids carrying inhibitory or inactivating oligomers and/or polymers of the above formula include those in which m is greater than about 10, those in which m is greater than about 25, those in which m is greater than about 50 and those in which m is greater than about 100.

Inhibitory oligomers and/or polymers of this invention typically are mixtures of more than one oligomer or polymer and can be mixtures containing both oligomers and polymers. Typically the mixture will have a distribution of oligomers or polymers of different n. Oligomers and/or polymers of the above formula can be obtained from commercial sources and or prepared by synthetic methods that are known in the art. Commercial or synthetic oligomers/polymers can be purified, if desired or needed, to remove impurities incompatible with the application of the oligomer or polymer. Commercial oligomers and/or polymers can be fractionated by methods known in the art to obtain a sub-fraction of oligomers and/or polymers. For example, a preparation which contains oligomers and polymers can be fractionated to provide a mixture of oligomers of selected lengths (e.g., those with n less than about 25).

For example, Breslow and Hulse, 1954 provide a synthesis of poly (vinylsulfonic acid) from vinyl sulfonic acid. The sodium salt of the polymer prepared was reported to have an estimated Mw of about 250,000. This material can be employed as a starting material for fractionation to obtain inhibitory materials of this invention. Additional methods for synthesis of poly vinylsulfonic acid or salts thereof are provided in C. E. Schildknect "Vinyl and Related Polymers" (John Wiley and Sons, Inc., N.Y.) 1952, pp. 643-648; V.V. Alderman and W. E. Hanford, U.S. Pat. No. 2,348,705 and G. D. Jones and G. E. Barnes, U.S. Pat. No. 2,515,714.

Similarly, solid or surface bound oligomers and/or polymers will typically be a mixture of more than one oligomer or polymer and can be mixtures containing both oligomers and polymers. Various methods for preparation of solid or surface bound inhibitors can be employed. In general, the solid or surface may contain reactive one or more chemical groups to which the linker group can be covalently attached. The attached linker group can contain one or more second reactive groups to which oligomers and/or polymers can be covalently attached. In a preferred embodiment, the oligomers and/or polymers are formed by in situ polymerization, where monomers are sequentially polymerized onto one or more of the second reactive groups of the linker to form the surface-bound oligomers and/or polymers.

In general, any solid that is compatible with the intended application, and that is compatible with the reactions which form the surface-bound oligomers and polymers can be employed. In specific embodiments, the solid is silica gel particles, glass beads, glass surfaces, cross-linked polystyrene, cross-linked PEG, microspheres, as well as plastic surfaces and/or plastic beads.

In situ polymerization of monomers can be performed, for example, using radical initiated polymerization methods (using catalysts, mediators, or light induced radical formation, for example). Controlled/living polymerization methods, as known in the art, such as ATRP methods, may also be employed. Scheme 1 illustrates polymerization methods by which immobilized materials of this invention may be prepared. Standard polymerization methods are illustrated on the left and controlled/living polymerization methods on the right. It may be beneficial to employ protected monomers the in situ polymerization. In addition, free oligomeric and polymeric materials may be covalently bonded to a surface, e.g., through reaction with a functionalized solid. Those of ordinary skill in the art in view of methods known in the art and the descriptions herein can prepare solid-bound materials of this invention.

The linker is a chemical moiety that provides for covalent bonding of the oligomers and/or polymers to the solid and for spacing of the oligomers and/or polymers from the surface. Solids derivatized with linker groups can be prepared by methods well-known in the art and linker derivatized solids may be available from commercial sources. The linker between the solid and the oligomer/or polymer is formed by a reactive linker precursor which allows for the formation of the desired bonds. To facilitate bonding to the solid, the linker precursor contains one or more first reactive groups which under appropriate reaction conditions bond to reactive groups on the surface of the solid. The linker precursor also has one or more second reactive groups to which covalent bonds to the oligomer and/or polymer can be formed. The second reactive groups may be latent reactive groups (e.g., protected reactive groups) that are activate for reaction after the linker is attached to the solid surface. The second reactive groups of the linker may simply have reactivity that is orthogonal to the reaction that bonds the linker to the solid (i.e., the second reactive groups do not react with the groups on the solid). The linker may, for example, be attached to the solid surface by ester, amide, thioester, and/or -0-Si bonds. The reactive precursor of the linker can for example have a first reactive group that is an acid, an activated ester, a thiol, an amine, an alkoxy silyl group. The second reactive group is any group to which an oligomer or polymer can be attached, but is preferably an unsaturated group, e.g., a terminal vinyl group, a styrene group, or any alpha-beta unsaturated carbonyl group (e.g., acrylamide) to which the unsaturated monomer of the oligomer or polymer (vinyl sulfonic acid, vinyl sulfuric acid or vinyl phosphonic acid) can be sequentially added by polymerization.

Oligomers and/or polymers of this invention can also be prepared by derivatization of oligomers and or polymers of vinyl alcohol, employing methods that are well known in the art.

Nucleases are enzymes that degrade nucleic acids, i.e. ribonucleic acids and or deoxyribonucleic acids. In specific embodiments, the oligomers and/or polymers of this invention inhibit and/or bind to ribonucleases (RNase) which selectively degrade ribonucleic acid (RNA). In other specific embodiments, the oligomers and/or polymers of this invention inhibit and/or bind to deoxyribonulcease (DNase) which selectively degrade deoxyribonucleic acid (DNA). In yet other specific embodiments, the oligomers and/or polymers of this invention inhibit and/or bind to nucleases that are non-specific and which can degrade both RNA and DNA. The nucleases, RNases and DNAases inhibited, inactivated or removed by the oligomers and/or polymers of this invention include both exonucleases and endonucleases.

RNases that can be inactivated, inhibited and/or removed using the materials of this invention include, among others, eukaryotic RNases (e.g., mammalian RNases or fungal RNases) and prokaryotic RNases. Specifically included are RNase A, RNase B, RNase C, RNase 1, RNase T1, bacterial RNase (e.g., those of *Escherichia coli*). U.S. Pat. 5,852,001 provides a description of the structural similarities of RNases referring to Beintema, 1987 and Wyckoff, 1971.

DNases that can be inactivated, inhibited and/or removed using the materials of this invention include, among others, DNase I and/or DNase II. Non-specific nucleases that can be inactivated, inhibited and/or removed using the materials of this invention include, among others, S1 nuclease and micrococcal nuclease.

The oligomers and/or polymers and surface-bound oligomers and/or polymers of this invention will typically be used in vitro to inactivate, inhibit and/or remove nucleases, including RNases and DNases. The term in vitro is used broadly herein to include the meaning of the term as it is broadly understood in the art and to include manipulation of biological materials ex vivo. Inactivation and/or inhibition is carried out by contacting a biological medium which may contain nucleases or into which nucleases may be intentionally or inadvertently introduced with one or more of the oligomers and/or polymers of this invention (as shown in the above formulas), The term "biological medium" is used broadly herein to encompass any liquid in which a biological reaction or assay can be carried out or performed which might be detrimentally affected by the presence of one or more active nucleases. The nuclease would typically be in the liquid, but could be adhered or immobilized to a surface.

Biological medium includes any buffers and reagents employed in biological reactions and assays. The inhibitors of this invention can, for example, be added along with reagents (e.g., prior to, or simultaneous with reagents) to inactivate or inhibit nucleases that might be present in a reaction mixtures. The inhibitors of this invention can, for example, be added to buffers to inactivate or inhibit nucleases therein. The surface-bound oligomers and/or polymers of this invention can, for example, be added to buffers to bind nucleases that may be present or inadvertently added to the buffer. The surface-bound oligomers and/or polymers of this invention can, for example, be added to a biological medium in which a reaction or assay is to be conducted to bind nucleases that may be present or have been inadvertently introduced. The solid to which the oligomers and/or polymers are bound can be readily removed from buffers and other biological media as desired or needed. The inhibitory oligomers and/or polymers can be bound to the internal surfaces (e.g., glass or plastic) of containers or other equipment (e.g., tubing, syringes, chromatography columns, etc.) in which biological media, including buffers, are stored or in which biological purifications, reactions and or assays are carried out. The oligomers and/or polymers of this invention can also be employed to inactivate or inhibit nucleases that have been immobilized or adhered on a solid. In this case a biological medium containing the inhibitory oligomers/and/or polymers would be contacted with the immobilized or adhered nuclease. The inhibitory oligomers and/or polymers or the solid-bound inhibitors of this invention can be added to a nuclease reaction to stop or arrest the further progress of the reaction.

The term "inhibit" as applied herein to the activity of nucleases means that the activity of at least one nuclease, e.g. at least one RNase or at least one DNase, is reduced in a sample to which an oligomer and/or polymer of this invention is added, compared to the activity in an analogous sample to which the oligomer and/or polymer is not added. Inhibition is not limited to complete inhibition or inactivation of a given nuclease. In a given application, it may be that some low level of nuclease activity can be tolerated that will not have a detrimental effect on the outcome of the reaction, purification and/or assay being performed. "Substantial inhibition" is achieved when the nuclease activity in a sample is below the level that is tolerable in a given application. The level of inhibition that is substantial will then depend upon the application in which inhibitors are employed. In contrast, the term inactivation is used when there is no detectable level of activity of a given nuclease. A nuclease that is inactivated need not be rendered irreversibly inoperative. Oligomers and/or polymers of this invention may exhibit inhibition of certain nucleases and inactivation of other nucleases. The term "inhibitory amount" as used in reference to the oligomers and/or polymers of this invention refers to the amount of an oligomer or polymer or the combined amount of a mixture of oligomers and/or polymers which is added to a biological medium containing one or more nucleases to observe inhibition (as defined above) of at least one of the one or more nucleases. Preferably, the oligomers and/or polymers are added in excess over the inhibitory amount.

The amounts or combined amounts of oligomers and/or polymers of this invention that are inhibitory toward a given nuclease or mixture of nucleases or which render one or more nucleases inactive can be readily determined by one of ordinary skill in the are with out expense of undue experimentation in view of the teachings herein and in view of what is generally known in the art.

The oligomers and/or polymers of this invention can be combined with any art-known nuclease inhibitor (that are not oligomers and/or polymers of this invention) to achieve a desired inhibitory effect on or inactivation of one or more nucleases.

Oligomers and polymer mixtures can be characterized and differentiated from other mixtures of oligomers and polymers by measurements of molecular weight and molecular weight distributions. The following defintions of molecular weight can be applied for such characterization (see: L. H. Sperling, Introduction to Physical Polymer Science, $2^{nd}$ Ed., Wiley New York (1992).)

Average Molecular Weight (M)=Average Number of Repeating Units n (or dp.)×the molecular weight or molar mass (Mi) of the repeating unit.

The number-average molecular weight ($M_n$) is the arithmetic mean, representing the total weight of the molecules present divided by the total number of molecules.

$$M_n = \frac{\sum_i N_i M_i}{\sum_i N_i}$$

Measurements that depend upon the number of molecules present depend on the number—average molecular weight. Mn can be determined using, for example, measurement of colligative properties, osmotic pressure and freezing point depression. End-group analysis can also provide a value for Mn.

The weight-average molecular weight (Mw) is defined, as is known in the art, by the equation:

$$M_w = \frac{\sum_i N_i M_i^2}{\sum_i N_i M_i}$$

The calculation of Mw requires the weight fraction, Wi, of each polymer molecule (of different weight) present. Weight fraction (Wi) of individual polymer molecules is the mass of each polymer molecule (NiMi) present divided by the total weight of the polymer:

$$\left(\sum_i N_1 M_i\right)$$

Light scattering and ultracentrifugation methods can be used to determine Mw.

The z-average molecular weight Mz, as is known in the art, is defined by the equation:

$$M_z = \frac{\sum_i N_i M_i^3}{\sum_i N_i M_i^2}$$

Gel permeation chromatography (also called size-exclusion chromatography, SEC or gel filtration chromatography) can be employed to determine molecular weight distributions of oligomers and polymers and can be used to obtain each of Mn, Mw and Mz (L. H. Sperling (1999) ACS Division of Polymeric Materials: Science and Engineering (PMSE) 81: 569.) Mass spectrometry, particularly MALDI, can also be employed to determine molecular weight distributions of oligomers and polymers (Creel, H., (1993) *Trends in Polymer Science*, "Prospects for the Analysis of High Molar Mass Polymers Using MALDI Mass Spectrometry," Elsevier, vol. 1 (11): 336-342.)

Characterization of the Inhibitor—RNase inhibitory activity was detected in commercial MES buffer and later found to be present in other commercially available ethane sulfonic acid buffers. We had shown that the byproduct responsible for RNase A inhibition would likely be anionic (Park and Raines, 2000) because the RNase A active site and RNA binding sites are cationic (pI=9.3) (Ui, 1971)). Thus, we chose to purify the inhibitor by anion-exchange chromatography. The low concentration of this inhibitor in MES buffer (~2 ppm) (park and Raines, 2000) necessitated purifying the contaminant from a large amount of MES buffer. Inhibitory activity of a number of different commercial lots of MES buffer was tested. All of the MES buffers tested exhibited substantial RNase A inhibition at low salt concentrations, but the inhibition per mole of MES did vary by 20-fold in different lots. The most inhibitory MES buffer (Sigma, 5.0 liters of a 0.50 M solution, pH 3.0) found was passed through a column containing 50 g of AG® 1-X8 anion-exchange resin (chloride form, Bio-Rad). No inhibitory activity was detected in the flow-through, indicating that the inhibitor was anionic and could be purified with anion-exchange chromatography. Likewise, no inhibitory activity was observed in a 0.1 M HCl wash of the column. The inhibitor was eluted from the anion exchange column with a 1-4 M linear gradient of HCl. Inhibitory activity was found in fractions corresponding to 1.7-4 M HCl. These fractions were pooled and evaporated to dryness, yielding 40 mg of material.

Identification of the Inhibitor—initial attempts to identify the inhibitor were based on the hypothesis that the inhibitor was a byproduct of ethanesulfonate buffer synthesis. In ethanesulfonate buffer synthesis, a nucleophile attacks 2-bromoethanesulfonic acid in $H_2O$ to yield the buffer product (FIG. 1). Hydrolysis or β-elimination of 2-bromoethanesulfonic acid could yield 2-hydroxyethanesulfonic acid (1) or vinylsulfonic acid (2). Nucleophilic attack of 2-hydroxyethanesulfonic acid on 2-bromoethanesulfonic acid or Michael addition to vinylsulfonic acid could generate diethanesulfonic acid ether (3). Indeed, all three of these byproducts were identified by NMR spectroscopy and mass spectrometry in the material purified from MES buffer (data not shown).

Figure 3:
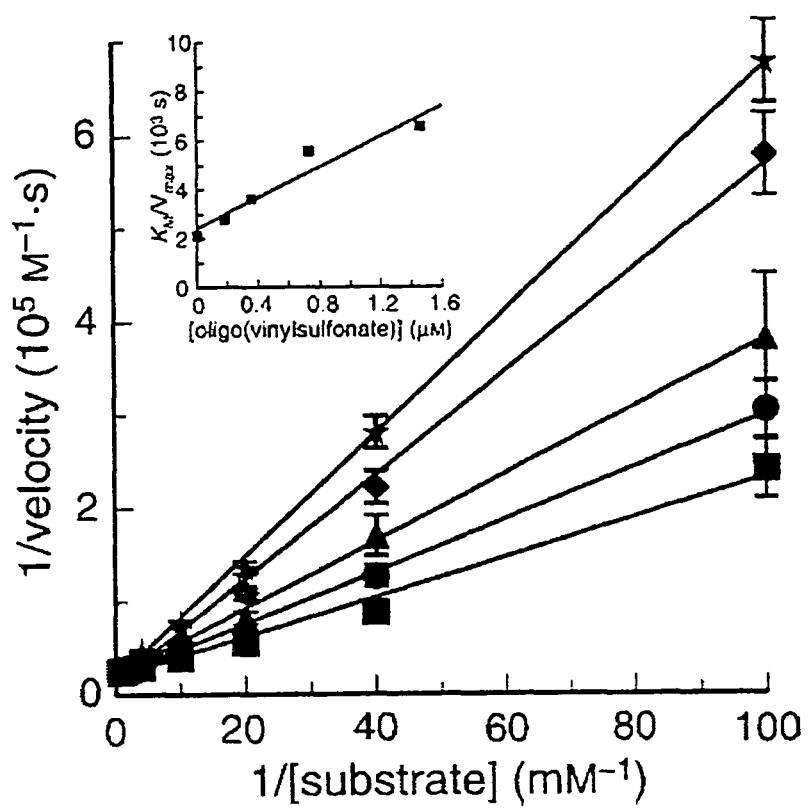
FIG. 3 is a graph illustrating the effect of commercial oligo(vinylsulfonic acid) on catalysis of poly(cytidylic acid) cleavage by ribonuclease A. Line-weaver-Burk plots are shown for five concentrations of oligo(vinylsulfonic acid): 0.0 (■), 0.35 (●), 0.7 (▲), 1.4 (◆), and 2.8 μM (*). Assays were performed at 25° C. in 50 mM imidazole-HCl buffer, pH 6.0, containing NaCl (0.10 M). Inset graph is a slope replot of the kinetic data.

Commercially available 2-hydroxyethanesulfonic acid (1) and vinylsulfonic acid (2) were tested as inhibitors of RNase A. Neither of these species was found to be a potent inhibitor in solutions of low salt concentration (FIG. 3). Diethanesulfonic acid ether (3) was synthesized (see: examples herein), but likewise failed to inhibit RNase A. Thus, the inhibitor in the buffer was not byproducts 1, 2, or 3.

An ultrafiltration concentrator (Vivaspin concentrator, 5,000 molecular weight cut-off, Vivascience AG, Hannover, Germany) was used to isolate and purify the inhibitor based on its affinity for RNase A. RNase A was mixed in doubly-distilled water ($ddH_2O$) with the inhibitory material that had been isolated by anion-exchange chromatography. The sample was subjected to centrifugation at 6,000 rpm for 15 min, washed with $ddH_2O$, and subjected again to centrifugation. Molecules that bind tightly to RNase A remained in the retentate, but non-binding impurities were washed into the eluate.

Matrix-assisted laser desorption ionization mass spectrometry of the retentate containing RNase A and the inhibitor revealed a heterogeneous mixture of small molecules of a molecular mass of about 900-2,000 g/mol.

The inhibitor was then separated from RNase A by adding a solution of ammonium acetate (0.10 M) to the mixture. After repeatedly concentrating and adding ammonium acetate solution to the mixture, unbound inhibitor moved to the eluate, and RNase A remained in the retentate. Matrix-assisted laser desorption ionization mass spectrometry of the free inhibitor revealed the same heterogeneous distribution of molecular mass with individual peaks separated by 108 g/mol (FIG. 3). Because the molecular mass of vinylsulfonic acid (2) is 108 g/mol, it seemed reasonable that the inhibitor was one or more oligomers of vinylsulfonic acid (OVS, 4). OVS could be a byproduct of ethanesulfonic acid buffer synthesis produced by ultraviolet light initiated radical-mediated polymerization of vinylsulfonic acid (3) (FIG. 3) (Breslow and Hulse, 1954). Characterization of Inhibition by OVS—Inhibition of RNase A activity was measured in 0.05 M imidazole-HCl buffer, pH 6.0, containing NaCl (0.10 M) using a commercially available OVS (Polysciences, Mr ~2,000,0-1.43 microM). OVS inhibition of RNase A is not time-dependent (data not shown). The addition of NaCl diminishes the OVS inhibition of RNase A, indicating that OVS is a reversible inhibitor of the enzyme. OVS inhibits RNase A at concentrations well below that of substrate; thus, inhibition by OVS is not attributed to its sequestering of RNA.

Double-reciprocal plots of RNase A catalytic activity versus the concentration of poly(C) at different OVS concentrations reveal that OVS inhibits RNase A in a competitive manner (FIG. 3). With poly(C) as a substrate, the apparent $K_i=(0.40\pm0.03)$ microM at 0.10 M NaCl. A replot of $(K_m/V_{max})_{app}$ versus [OVS] reveals a linear dependence, which is indicative of simple competitive inhibition (Cleland, 1977).

Figure 4A:
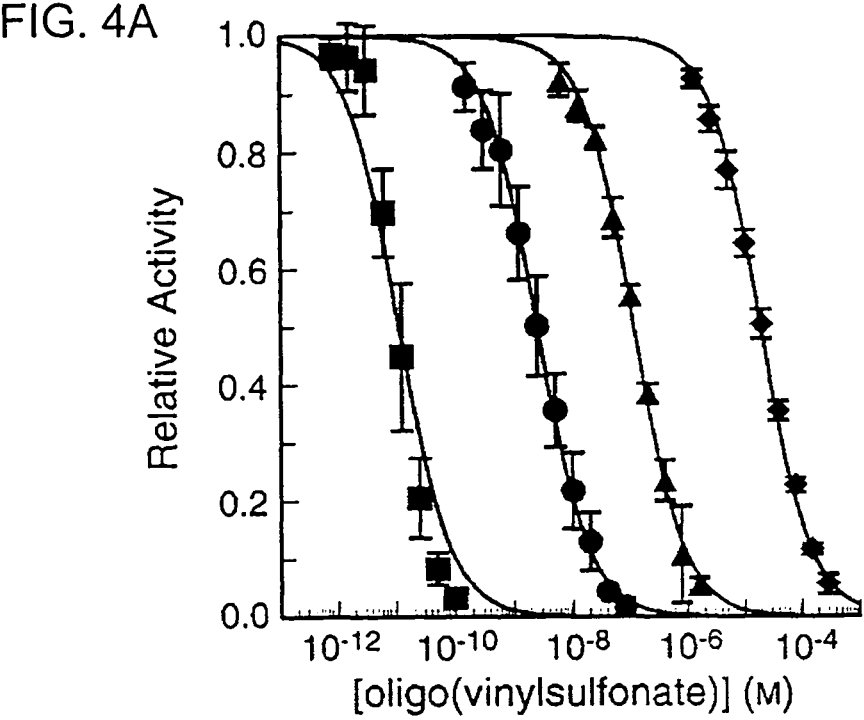
FIGS. 4A and 4B illustrate the salt dependence of commercial oligo(vinylsulfonic acid) inhibition of catalysis of 6-FAM~dArUdAdA~6-TAMRA cleavage by ribonuclease A.

Salt Dependence of Inhibition by OVS—The Ki of OVS was measured at four different salt concentrations in 50 mM imidazole-HCl buffer, pH 6.0. Because OVS inhibits RNase A in a competitive manner, a sensitive fluorescent assay was used to assess inhibition by OVS. OVS inhibition of RNase A is highly salt-dependent (FIG. 4A). At 0 M NaCl, OVS inhibits catalysis by RNase A with an astonishingly low inhibition constant of $K_i=(11\pm2)$ pM. In the absence of added NaCl, the inhibition curve was fitted to a tight-binding inhibitor equation, yet the curve still exhibits some cooperativity. At 0.10 M NaCl, OVS inhibits RNase A with an inhibition constant of $K_i=(120\pm10)$ nM. (In theory, the value of Ki for a competitive inhibitor should be independent of the substrate used in the assay. Yet the observed value of Ki, for OVS is 3-fold higher when poly(C) rather than 6-FAM~dArUDAdA~6-TAMRA is the substrate for RNase A. This effect of polymeric substrates has much precedence and several explanations have been proposed (Nelson and Hummel, 1961; Sela, 1962; Richards and Wyckoff, 1971).

Figure 5:
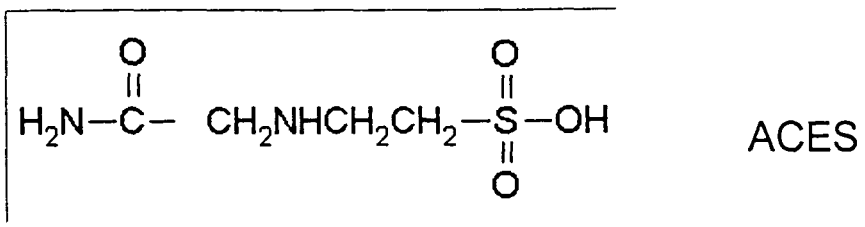
FIG. 5 illustrates the structures of several ethanesulfonate buffer components.
Figure 5:
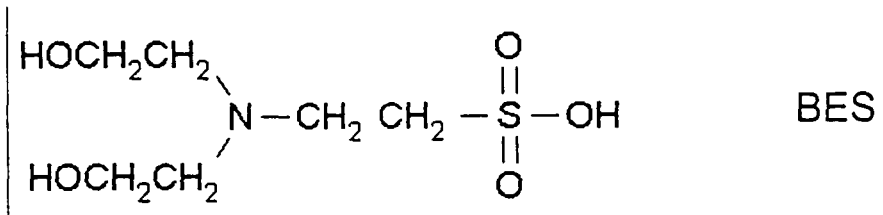
Figure 5:
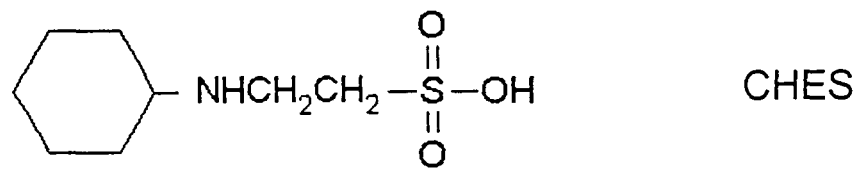
Figure 5:
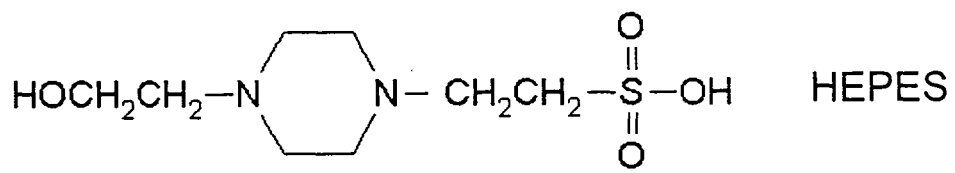
Figure 5:
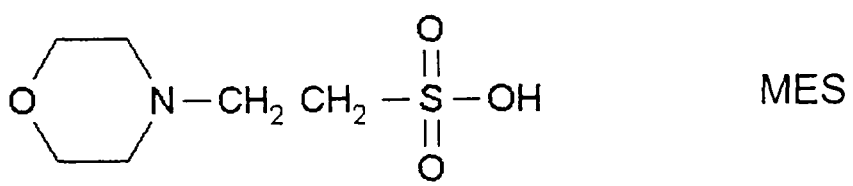
Figure 5:
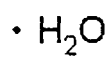
Figure 5:
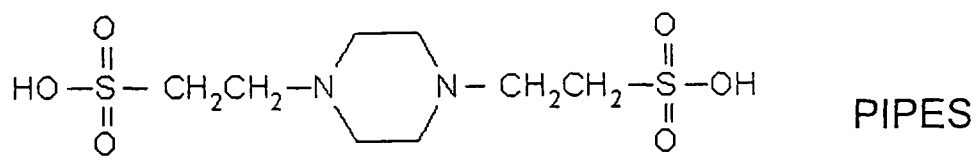

According to polyelectrolyte theory, the slope of a plot of log(Ki) versus log ([Cation]) reveals the number of Coulombic interactions between a ligand and a polyanion (28). OVS makes on average 7.8 ionic interactions with RNase A (FIG. 5B). Poly(vinylsulfuric acid), an OVS analog, exhibits a similar salt dependence (data not shown).

Figure 4B:
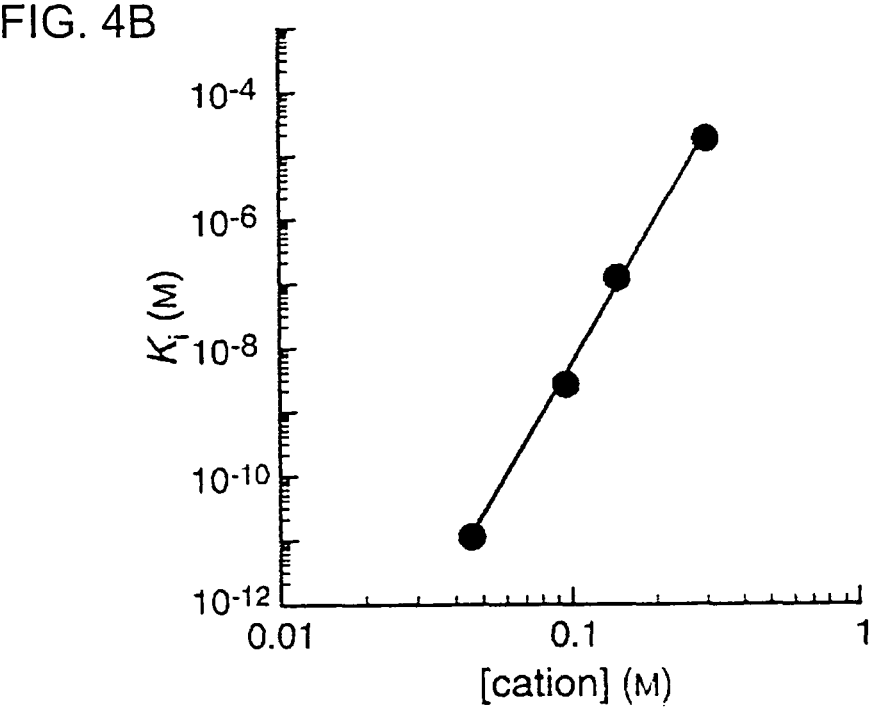

OVS inhibition of RNase A follows a simple competitive model (FIG. 3). Because OVS (~2000 g/mol) has on average only 18 monomer units per molecule, it is on the cusp of consideration as a polyelectrolyte (Record et al. 1976). Nonetheless, a double-log plot of Ki versus [Cation] indicates that OVS forms 7.8 Coulombic interactions with RNase A (FIG. 4B). The inhibition of RNase A by poly(vinylsulfuric acid) (~170,000 g/mol) shows a similar salt dependence (data not shown).

The number of Coulombic interactions between OVS and RNase A is in agreement with a previous report (Record et al., 1976) that single-stranded DNA forms 7 Coulombic interactions with RNase A. This indicates that OVS likely saturates the same phosphoryl group binding subsites as does a single-stranded nucleic acid (See, FIG. 1 in Smith et al. 2003).

Polyanions are reported to be effective inhibitors of RNase A (Richards and Wyckof, 1971). Heparin, tyrosine-glutamate copolymers, and many different polysulfates and polyphosphates have been shown reported to inhibit catalysis by the enzyme (Sela, 1962; Zollner and Felig, 1953; Heymann et al., 1958). OVS, like PVP and PVOS, is similar to a nucleic acid back-bone in having anionic non-bridging oxygen atoms. In addition, the phosphorous atoms in a nucleic acid and alternating sulfur atoms in OVS are separated by five other atoms. However, there is a major difference between OVS and a nucleic acid. With its three non-bridging oxygens per monomer unit, OVS provides many more opportunities to form strong hydrogen bonds than does a nucleic acid. Pyrophosphate-linked ribonuclease inhibitors also display extra non-bridging oxygens, which probably enhance their affinity for RNase A (Russo and Shapiro, 1999).

OVS compares favorably with the most potent known small-molecule inhibitor of RNase A, the pyrophosphate-linked oligo-nucleotide, pdUppA-3'-p (Russo et al., 2001). Under similar buffer conditions with 0.10 M NaCl, each has a Ki near 120 nM. Yet, unlike pdUppA-3'-p, OVS is simple to prepare and is extremely stable.

OVS is thus useful in preventing incidental ribonuclease contamination and RNA degradation in experiments involving RNA. Indeed, poly(vinylsulfuric acid), an OVS analog, has been added to experiments involving the isolation of mRNA (Cheng et al., 1974) or cell-free translation (Mach et al., 1968). Other enzymes are known to be inhibited by poly (vinylsulfonic acid). For example, poly(vinylsulfonic acid) inhibits catalysis by RNA polymerase and reverse transcriptase (Chambon et al., 1967; Althaus et al., 1992).

RNase A Inhibition by OVS Analogs—To assess the importance of the sulfonic acid group for RNase A inhibition, poly(vinylphosphonic acid) (PVP) and poly(vinylsulfuric acid) (PVOS) were also tested for inhibition of ribonucleolytic activity in the fluorescent assay in the examples herein. These analogs are also good inhibitors of RNase A, but are slightly less effective than is OVS (Table I). The average molecular masses of PVP and PVOS were 20,000 and 170,000 g/mol, respectively (values obtained from the manufacturer.) Mass spectrometry indicates that strong bonding of OVS oligomers involved binding of about nine monomer units. This suggests that more than one RNase could bind to OVS oligomers of n greater than 9. In commercial OVS (~2,000 g/mol n=19) two RNase A molecules could tightly bind per oligomer chain. Each molecule of PVP or PVOS could be expected to tightly bind to more than two RNase. To allow a more direct comparison of inhibition by OVS, PVP, and PVOS, the data listed in Table I are in units of mass rather than in units moles.

TABLE I

Inhibition of ribonuclease A catalysis by commercial oligo(vinylsulfonic acid) and its phosphonic acid and sulfuric acid analogs.

| Inhibitor | $K_i^a$ µg/ml |
| --- | --- |
| Oligo(vinylsulfonic acid) | 0.24 ± 0.02 |
| Poly(vinylphosphonic acid) | 0.35 ± 0.02 |
| Poly(vinylsulfuric acid) | 0.38 ± 0.06 |

$^a$Values of $K_i$ were obtained in 0.05 mM imidazole-HCl buffer, pH 6.0, containing NaCl (0.10 M).
Values of $K_i$ are in units of µg/ml to account for the different average molecular mass of each oligomer or polymer.

The OVS was difficult to separate from other anionic byproducts of ethane-sulfonic acid buffer synthesis (FIG. 1). OVS has no distinct properties that allow it to be detected during purification. NMR spectroscopy failed to detect OVS in the material purified from MES, because less than 5% (by weight) of that material was OVS. However, mass spectrometry did enable the identification of OVS in MES buffer. Specifically, oligomers of 9-17 units were detected. It is probable that oligomers shorter than 9 units in length are also present in MES buffer, but these were not observed after anion-exchange chromatography and affinity purification. Because purification of the inhibitor was monitored by RNase A inhibition assays, OVS oligomers having fewer than about 9 units are probably less-effective inhibitors of RNase A.

Buffer purification—Because of the low levels of OVS present purification of the buffer was problematic. Less than 2 mg of OVS was isolated from 0.5 kg of the most contaminated MES buffer tested. OVS has been found to be a common contaminant of ethanesulfonic acid buffers, such as those containing ACES, BES, CHES, HEPES, MES, PIPES and mixtures thereof. See FIG. 5 for the chemical structures of exemplary ethanesulfonic derivatives used in buffers. It is believed that OVS is a byproduct of synthesis of the ethanesulfonic acid derivative of the buffer (See FIG. 1).

Although present in very low concentrations (typically up to 10's of ppms), in buffers, OVS has been identified herein as a potent inhibitor of RNase A. All commercial lots of MES buffer tested contained RNase inhibitory activity believed due to the presence of OVS. Other ethane sulfonic acid buffers, including BES, CHES and PIPES were also found to contain the OVS inhibitors. The amount of inhibitor in MES buffers was found to vary from lot to lot by up to a 20-fold variation. OVS is believed to be a byproduct of synthesis of the ethane sulfonic acid buffer, e.g., MES (See: FIG. 1). It is likely that all ethanesulfonic acid buffers contain OVS and that the amount will vary from lot to lot and will be, at least in part, dependent on the handling (storage conditions, etc.) of each individual sample of buffer.

The presence of such an inhibitor in these widely used biological buffers is undesirable, particularly when the buffer is to be employed for assays of RNase activity, assays which employ active RNase as a component or reagent and for any experiments which study or require active RNase.

The RNase inhibitor in these ethane sulfonic acid buffers can be reduced or removed by passage of the buffer through an anion exchange resin column. Preferably passage of the buffer through the anion exchange resin column results in a purified buffer that does not contain OVS RNase inhibitors. However, passage of the buffer through an anion exchange column may also be employed to reduce the level of such inhibitors in the buffer below a desired level needed for a given buffer application.

The anion exchange resin employed is preferably a strong base anion exchange resin. The anion exchange resin employed is preferably crosslinked and more preferably has about 4% to about 10% cross-linking. An anion exchange resin with 8% crosslinking has been used successfully to remove OVS oligomers from MES. In a specific embodiment, AG®1-X8 anion exchange resin (Bio-rad) is employed in the purification of ethane sulfonic acid buffers. One of ordinary skill in the art can in view of the teachings herein and what is known in the art select an anion exchange resin that is suitable for removal of the RNase inhibitory species in the buffer. A given anion exchange resin, its ion form (e.g., Cl⁻ form), the extent of crosslinking, the amount of resin employed to purify a given amount of buffer can be readily selected for application to the purification of these buffers based on knowledge in the art and/or routine experimentation. Further, manufactures of anion exchange resins often provide selection criteria and or comparisons in their product literature which allow the selection of an anion exchange (or other) resin that is functionally equivalent to a resin that is known or has been tested as suitable for a given application. Anion-exchange resins are available from a number of commercial suppliers including Biorad.

Most generally, the RNase inhibitory species, OVS, are removed from ethanesulfonic acid buffers known or shown to contain such inhibitors by contacting the buffer with a suitable anion exchange resin which binds the OVS species. Conveniently, the buffer is contacted with the resin by passage of buffer through a column containing the resin. Alternatively, resin may be added to the buffer, optionally agitated, and thereafter the resin is separated from the buffer resulting in removal of the RNase inhibitory OVS species. The method of this invention is generally applicable to removal of OVS species, particularly those that are RNase inhibitory, from any ethane sulfonate buffer that may contain these species. The amount of resin employed generally depends upon the amount of buffer to be purified and the capacity of the resin. It is preferred that a sufficient amount of resin is employed and/or the contact time of resin and buffer is such that the buffer eluting from a column (or buffer separated from resin) does not contain measurable levels of the inhibitors. The buffer may be tested before purification to assess the presence or level of inhibitor that is present, which information may be useful in selecting the type or amount of resin to use. The buffer may be tested after contact with the resin to assess the presence or level of inhibitor present. The inhibitor can be detected or measured employing RNase inhibition assays known in the art. The inhibitor can be detected or its amount measured, in particular, by the fluorescence assay of the inhibition of ribonucleolytic activity described in the examples herein.

The presence of OVS in all lots of MES buffer tested herein and in many other ethanesulfonic acid buffers is a concern. The amount of OVS varies from lot to lot, and thus, some lots of buffers could contain sufficiently high concentrations of OVS to detrimentally affect the results of experiments performed using the buffer. All ethansulfonic acid buffers are thus preferably purified by the method described herein with anion exchange resin prior to their use in assays of enzymatic activity.

MES buffer has been the buffer of choice in assays of the catalytic activity of RNase A, as the pKa of MES buffer (pKa=6.15) (Good et al., 1966) is near the pH of maximal activity (pH=6.0) (del Rosario and Hammes, 1969). Many RNase A assays are performed in the presence of 0.10 M NaCl at which the Ki of OVS is 120 nM (FIG. 4A). OVS concentration in many lots of MES buffer tested was near 2 ppm. In 0.10 M MES buffer, the concentration of OVS could be near 0.2 microM, which is greater than its Ki value. Historically, RNase A has been reported to have a bell-shaped salt-rate profile with an optimum salt concentration near 0.1 M NaCl (Edelhoch and Coleman, 1956; Irie, 1965). This observed bell shape may be an artifact because of contaminating OVS in MES buffer. Indeed, the salt-rate profile of RNase A has been measured recently in bis-tris buffer, revealing that ribonucleolytic activity increases to the diffusion limit as salt concentration decreases (Park and Raines, 200; Park and Raines, 2001; Park and Raines, 2003).

Figure 6A:
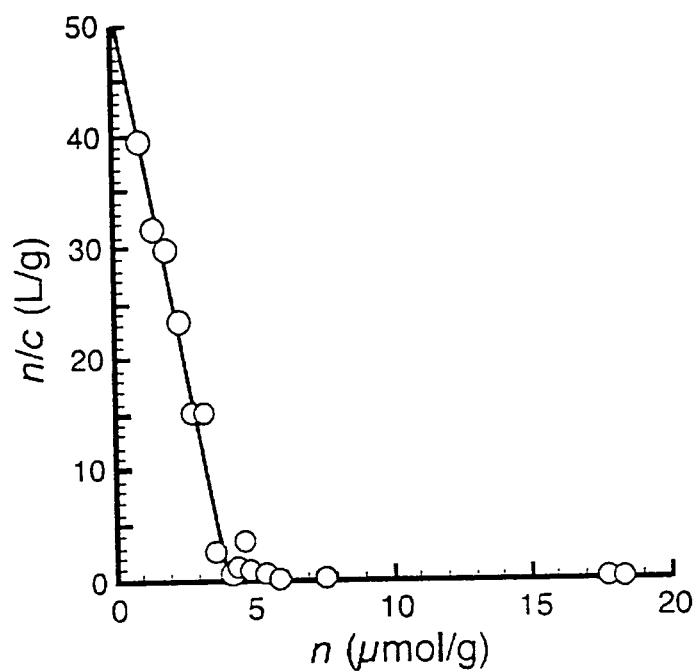
FIGS. 6A-C are graphs which illustrate binding of RNase A to immobilized poly(vinylsulfonic acid).

Immobilized poly(vinylsulfonate)—PVS-coated surfaces are found to sequester ribonuclease (as demonstrated by sequestration of fluorescently-labeled ribonuclease, data not shown). For example, PVS-coated silica was shown to remove a ribonuclease that had been added to a solution. A Scatchard plot of the data is curvilinear (FIG. 6A) as expected for the binding of a ligand to a lattice of sites. The equilibrium dissociation constants for the tightest binding sites were determined from the limiting slope of the Scatchard plot. The PVS-coated silica has 4.1 μmol/g of tight-binding sites for RNase A and $K_d$=80 nM for these sites. This $K_d$ value is in agreement with the inhibition constant observed using free PVS ($K_i$=120 nM). In the presence of PVS-coated silica with excess tight-binding sites, residual ribonucleolytic activity is not detectable (i.e., <0.01%).

PVS-coated surfaces also sequester ribonuclease quickly. The enzymatic activity of an added ribonuclease was measured at known times after exposure to PVS-coated silica in which the number of tight-binding sights was only twofold greater than the amount of ribonuclease. Half of the ribonuclease was bound within 1 min; maximum binding occurred within 1 h. In contrast, an acrylamide-coated silica control did not remove any ribonuclease after 4 h of contact with a ribonuclease-containing solution. PVS-coated surfaces far exceed the capacity and affinity for nucleases of other known surfaces.

For comparison, in the most effective prior example, poly [2'-O-(2,4-nitrophenyl)] poly(A) [DNP— poly(A)] was attached to acrylic beads (Rahman, M. H.; Kang, I.; Waterbury, R. G.; Narang, U.; Bright, F. V.; Wang, J. H. Anal. Chem. 1996, 68, 134-138). This material has 0.017 µmol/g of binding sites for RNase A (which is 240-fold less than PVS-coated silica) and $K_d$=0.41 µM in a solution of low salt concentration (which is $3.7 \times 10^4$-fold greater). Accordingly, the adsorptive efficacy of PVS-coated silica exceeds that of other known surfaces by $10^7$ fold.

PVS-coated surfaces can be regenerated and reused many times. For example, PVS-coated silica was incubated with RNase A such that the amount of free RNase A was <0.5%. After the incubation, nearly 100% of the bound RNase A was eluted by washing with 1.0 M NaCl. This incubation/elution cycle was repeated a total of five times with no detectable change in the amount of ribonuclease sequestered or released.

PVS-coated surfaces can bind various RNases. For example, PVS-coated surfaces bind the most prevalent human ribonuclease, RNase 1. Under conditions similar to those used for RNase A, a solution of human RNase 1 is >99.5% bound by PVS-coated silica.

PVS-coated surfaces prevent RNA degradation in solution that contain one or more nucleases or which are or may become contaminated with one or more nucleases. For example, PVS-coated surfaces prevent RNA degradation in buffer contaminated intentionally with nucleases from human skin.

Various surfaces can be coated with PVS by chemical synthesis, such as methods described herein or by routine adaptation of those methods. It is believed that such surfaces extract nucleases from solutions preventing undesired detrimental effects from those nucleases. PVS-coated surfaces are believed to quickly and completely remove nucleases, particularly those present at contaminant levels (such as those present by inadvertent contamination from human skin). PVS-coated surfaces can be used repeatedly. Nucleases can be removed from the surfaces, e.g., by washing with aqueous salt solutions (e.g., 1 M NaCl), and reused to extract additional nucleases. PVS-coated surfaces have many advantages over other means and methods known in the art to sequester nucleases and as a result can be used in a variety of applications to preserve the integrity of DNA and RNA.

The preparation of PVS-coated surfaces (surfaces carrying immobilized PVS) is exemplified herein on silica gel and glass slides. More specifically, PVS is immobilized on surfaces that have been modified to display amino groups (Lesaicherre, M. L.; Uttamchandani, M.; Chen, G. Y.; Yao, S. Q. Bioorg. Med. Chem. Lett. 2002, 12,(16), 2079-2083). Reaction of the surface amino groups, for example with acryolyl chloride, generated polymerizable groups immobilized on the surface, e.g., acrylamide groups. For example, electron-deficient alkenes immobilized on the surface will undergo facile polymerization. Radical-mediated polymerization of vinylsulfonate ($CH_2$=$CHSO_3^-$) or related olefinic species can then be conducted on the surfaces carrying polymerizable groups, such as electron-deficient alkenes. The resulting surfaces carrying polymerized inhibitors can be washed until free inhibitor is no longer detectable with a sensitive assay for ribonuclease inhibition.

Preparation of PVS-coated (or immobilized) surfaces is exemplified herein by an in situ polymerization method. Those of ordinary skill in the art will appreciate that other means for directly or indirectly (through a linker) coupling of oligomers and/or polymers of this invention to surfaces are available in the art and can be employed in the practice of this invention.

Those of ordinary skill in the art will appreciate that the oligomers and polymers that function for inhibition of nucleases can be immobilized on surfaces, such as silica gel and glass, employing methods that are known in the art or in view of methods described herein in view of what is known generally in the art.

Surfaces carrying immobilized oligomeric or polymeric nuclease inhibitors of this invention are exemplified by PVS-coated surfaces. Surfaces carrying other inhibitor oligomers and/or polymers of this invention can be applied as exemplified herein for sequestration of nucleases and prevention of the undesired degradation of nucleic acids.

The oligomeric and polymeric inhibitors of this application and surfaces carrying immobilized oligomers and polymers of this invention can be applied in various ways to remove or inhibit nucleases. For example, surfaces coated with inhibitor, particularly PVS-coated surfaces, can be useful in many contexts (see: Raines (1998) supra; Narang, U.; Rahman, M. H.; Wang, J. H.; Prasad, P. N.; Bright, F. V. Anal. Chem. (1995) 67, 1935-1939; and Rahman et al. (1996) supra)). For example, the addition of inhibitor-coated resin, followed by filtration or centrifugation, can be used to remove nucleases from solution. Alternatively, inhibitor-coated glassware or plasticware can adsorb contaminating nuclease, thereby providing safe long-term storage for valuable nucleic acids.

All numerical ranges recited in the specification are intended to encompass all subranges thereof and each numerical member of the range. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomers and enantiomer of the compound described individual or in any combination. For each compound and formula described herein it is intended that all isotopic variants of elements in that compound and all isotopic variants of any variables or chemical elements in the formula are encompassed by this disclosure. For example, any and all hydrogens of compounds and or formulas herein can be replaced with deuterium and or tritium. As is known in the art, isotopic variants can be useful in chemical analysis (e.g., NMR methods and mass spectrometry) and in biological/chemical experimentation. Specific names of compounds are intended to be exemplary, as it is known that one of ordinary skill in the art can name the same compounds differently.

The invention illustratively described herein suitably may be practiced in the absence of any element or elements, limitation or limitations which is not specifically disclosed herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

All references cited herein are incorporated by reference herein to the extent that they are not inconsistent with the teachings herein. References are cited herein to provide additional details of classes and types of RNases known in the art that can be inhibited or removed employing the methods herein, to provide additional details of synthetic methods for preparation and/or isolation and/or purification of inhibitors herein, to provide additional details of applications of the inhibitors herein; to provide additional details of art-known methods for the determination of properties of the inhibitors herein, particularly molecular weight measurements and assessment of polydispersity of oligomers and mixtures thereof.

Those of ordinary skill in the art will appreciate that materials, methods, techniques, assays and devices other than those specifically disclosed herein can be readily employed in the practice of this invention without resort to undue experimentation. The ordinary skilled artisan will also know of the existence of art-recognized equivalents of materials, methods, techniques, assays and devices specifically disclosed herein and appreciate that these art-recognized equivalents can be employed in the practice of this invention. All such art-recognized equivalents are intended to be encompassed by this invention.

EXAMPLES

Materials and Methods:

Poly(cytidylic acid) (poly(C)) was obtained from Midland Certified Reagents (Midland, TX). Poly(C) was purified prior to use by precipitation in aqueous ethanol (70% v/v). The fluorogenic ribonuclease substrate 6-FAM~dArUdAdA~6-TAMRA (where 6-FAM is a 5'-6-carboxyfluorescein group and 6-TAMRA is a 3'-6-carboxytetramethyl-rhodamine group) was obtained from Integrated DNA Technologies (Coralville, Iowa). Oligo(vinylsulfonic acid) ($M_w$~2,000) and poly(vinylphosphonic acid) ($M_r$~20,000) were obtained from Polysciences (Warrington, PA). Vinylsulfonic acid and poly(vinylsulfuric acid) ($M_r$~170,000) were obtained from Aldrich. All other commercial chemicals and biochemicals employed were of reagent grade or better and were used without further purification.

UV absorbance measurements were made with a Cary Model 3 spectrophotometer (Varian, Palo Alto, Calif.). Fluorescence measurements were made with a QuantaMaster 1 photon counting fluorometer equipped with sample stirring (Photon Technology International, South Brunswick, N.J.). Synthesis of Diethanesulfonic Acid Ether—2-Mercaptoethylether (5.0 g, 36.2 mmol, Caution: Stench!, Aldrich) was dissolved in glacial acetic acid (5 ml). The resulting solution was then cooled to 0° C. While stirring at 0° C., a mixture (50:45 ml) of glacial acetic acid and aqueous hydrogen peroxide (30% v/v) was added to the 2-mercaptoethylether solution dropwise over 1 h. After addition, the reaction mixture was heated at 60° C. for 90 min. The solvent was then removed from the reaction mixture under reduced pressure. Residual acetic acid was removed by addition of toluene which enabled formation of azeotropes of low boiling point. The yellow oil resulting from solvent removal was used without further purification (spectral data: 1H NMR (300 MHz, $D_2O$) δ2.88 (t, J=7.1 Hz, 4H), 2.17 (t, J=7.0 Hz, 4H) ppm; mass spectrometry (electrospray ionization) m/z 232.9791 ($M^-H$ [$C_4H_9O_7S_2$]=232.9795)). Production of RNase A—Plasmid pBXR (delcardayre et al., 1995) directs the production of RNase A in *Escherichia coli*. RNase A was produced and purified as described previously (Kim, and Raines, 1998) with the following modifications. *E. coli* strain BL21 (DE3) transformed with pBXR was grown to an optical density of 1.8 at 600 nm in terrific broth medium containing ampicillin (0.40 mg/ml). The expression of the RNase A cDNA was induced by the addition of isopropyl-1-thio-β-D-galactopyranoside to 0.5 mM. Cells were collected 4 h after induction and lysed with a French pressure cell. Inclusion bodies were recovered by centrifugation and resuspended for 2 h in 20 mM Tris-HCl buffer, pH 8.0, containing guanidine-HCl (7 M), dithiothreitol (0.10 M), and EDTA (10 mM). The protein solution was diluted 10-fold with aqueous acetic acid (20 mM), subjected to centrifugation to remove any precipitate, and dialyzed overnight against aqueous acetic acid (20 mM). Any precipitate was removed again by centrifugation. The supernatant was diluted to a protein concentration near 0.5 mg/ml in a refolding solution of 0.10 M Tris-HCl buffer, pH 8.0, containing NaCl (0.10 M), reduced glutathione (1.0 mM), and oxidized glutathione (0.2 mM). RNase A was refolded for 16 h and concentrated by ultrafiltration with a YM10 membrane (Mr 10,000 cut-off, Millipore, Bedford, Mass.). Concentrated RNase A was applied to a Superdex G-75 gel filtration fast protein liquid chromatography column (Amersham Biosciences) in 50 mM sodium acetate buffer, pH 5.0, containing NaCl (0.10 M) and $NaN_3$ (0.02% w/v). Protein from the major A280 peak was collected and applied to a Mono S cation-exchange fast protein liquid chromatography column. RNase A was eluted from the column with a linear gradient of NaCl (0.2-0.4 M) in 50 mM sodium acetate buffer, pH 5.0. Protein concentration was determined by UV spectroscopy using $\epsilon$=0.72 ml $mg^{-1}$ $cm^{-1}$ at 278 nm (Sela et al., 1957).

Inhibition of RNase A Catalysis—Inhibition of ribonucleolytic activity was measured by using either poly(C) or a fluorogenic substrate. The total cytidyl concentration of poly (C) was quantitated using $\epsilon$=6,200 $M^{-1}$ $cm^{-1}$ at 268 nm (Yakovlev et al., 1992). The cleavage of poly(C) was monitored by the decrease in ultraviolet hypochromicity. The Δε value for this reaction calculated from the difference in molar absorptivity of the polymeric substrate and the mononucleotide cyclic phosphate product was 2,380 $M^{-1}$ $cm^{-1}$ at 250 nm (delcardayre and Raines, 1994). Assays were performed at 25° C. in 50 mM imidazole-HCl buffer, pH 6.0, containing NaCl (0.10 M), poly(C) (10 microM-1.5 mM), OVS (0-1.43 microM), and enzyme (1.0 nM).

Molar values of OVS were calculated by using the number average molecular mass (Mn) of 2,000 g/mol (value provided by the manufacturer and said to be measured by GPC, Polysciences.) It is possible that an oligomer of this size could bind two enzymes. Thus, the actual Ki values could be 2-fold higher. Kinetic parameters were determined from initial velocity data with the program DELTA-GRAPH 4.0 (DeltaPoint, Monterey, Calif.). For the fluorescence assay, the inhibition of ribonucleolytic activity was assessed at 25° C. in 2.0 ml of 50 mM imidazole-HCl buffer, pH 6.0, containing NaCl (0-0.25 M), 6-FAM~dArUdAdA~6-TAMRA (60 nM), and RNase A (1-5 pM) as described previously (Kelemen et al., 1999; Park et al., 2001). Fluorescence (F) was measured using 493 and 515 nm as the excitation and emission wavelengths, respectively. The value of ΔF/Δt was measured for 3 min after the addition of RNase A. An aliquot of inhibitor (I) dissolved in the dissolved in the assay buffer was added next, and $\Delta F/\Delta t$ was measured in the presence of the inhibitor for 3 min. The concentration of inhibitor in the assay was doubled repeatedly in 3-min intervals. Excess RNase A was then added to the mixture to ensure that about 10% substrate had been cleaved prior to completion of the inhibition assay. Apparent changes in ribonucleolytic activity due to dilution were corrected by comparing values to an assay in which aliquots of buffer were added to the assay. Values of Ki were determined by non-linear least squares regression analysis of data fitted to Equation 1 (Kelemen et al., 1999; Park et al., 2001).

$$\Delta F/\Delta t=(\Delta F/\Delta t)_0(K_i/(K_i+[I])) \quad \text{(Eq. 1)}$$

At 0 M NaCl, the enzyme concentration ([E] total) caused a significant depletion in inhibitor concentration, thus the data were fitted to Equation 2, which describes tight-binding inhibition (Henderson, 1972).

$$\Delta F/\Delta t=((\Delta F/\Delta t)_0/2[E]_{total})\{[(K_i+[I]-[E]_{total}]^2+ 4K_i[E]_{total})^{1/2}-(K_i+[I]-[E]_{total})\} \quad \text{(Eq. 2)}$$

In Equations 1 and 2, $(\Delta F/\Delta t)_0$ was the ribonucleolytic activity prior to inhibitor addition.

Purification of Commercial Buffers—MES buffer was found to inhibit catalysis by RNaseA, especially in solutions of low salt concentration. Additionally, other ethanesulfonic acid buffers such as BES, CHES, and PIPES, were found to exhibit similar inhibition of RNase A. Buffer purification was developed using MES buffers. The inhibitory activity of a number of different commercial lots of MES buffer was assessed. All MES buffers tested exhibited substantial RNase A inhibition at low salt concentrations, but the inhibition per mole of MES was found to vary by up to 20-fold in different lots. Passage of MES buffer through an anion-exchange chromatography column was found to remove the inhibitor.

More specifically, 0.5 kg of the most inhibitory MES buffer (5.0 L of a 0.50 M solution, pH 3.0, Sigma Chemical, St. Louis, Mo.) was passed through a column containing 50 g of AG 1×8 anion exchange resin (chloride form, Biorad, Hercules, Calif.). The flow through of the column can optionally be recrystallized from water to yield purified MES buffer that is inhibitor-free.

Identification of the Inhibitor—Inhibitory activity was eluted from the anion exchange column used to purify the MES buffer. Initial 0.1 M HCl wash of the column did not result in elution of inhibitory activity. The inhibitory activity was, however, eluted using a 1-4µ linear gradient of HCl. Inhibitory activity was observed to be present in fractions corresponding to 1.7-4µ HCl. These fractions were pooled and evaporated to dryness (yield from 5 L of 0.50µ, pH 3.0 MES buffer above) was 40 mg of material). NMR and MS methods identified the presence of 2-OH ethanesulfonic acid, vinyl sulfonic acid and diethanesulfonic acid in the dried materials. All three of these products were obtained from commercial sources or synthesized (see above) and tested for RNase A inhibition. None of these three materials was found, when tested, to exhibit inhibitory activity.

The inhibitory material was then isolated based on possible binding affinity for RNase A. RNase A (10 mg) was mixed in dd $H_2O$ (double distilled $H_2O$, 10 mL) and 10 mg of the dried inhibitory material that had been eluted from the anion exchange column on purification of MES buffer. This sample was subjected to treatment with a Vivaspin concentrator (ultracentrifugation concentrator, 5,000 molecular weight cut-off, Vivascience AG, Hannover, Germany). The sample was again subjected to centrifugation at 6,000 rpm for 15 min., washed with dd $H_2O$ (3×15 mL) and again centrifuged. Molecules that bind tightly to RNase remain in the retentate containing RNase A whereas nonbinding (or low affinity binding) species are washed into the eluate.

Figure 2:
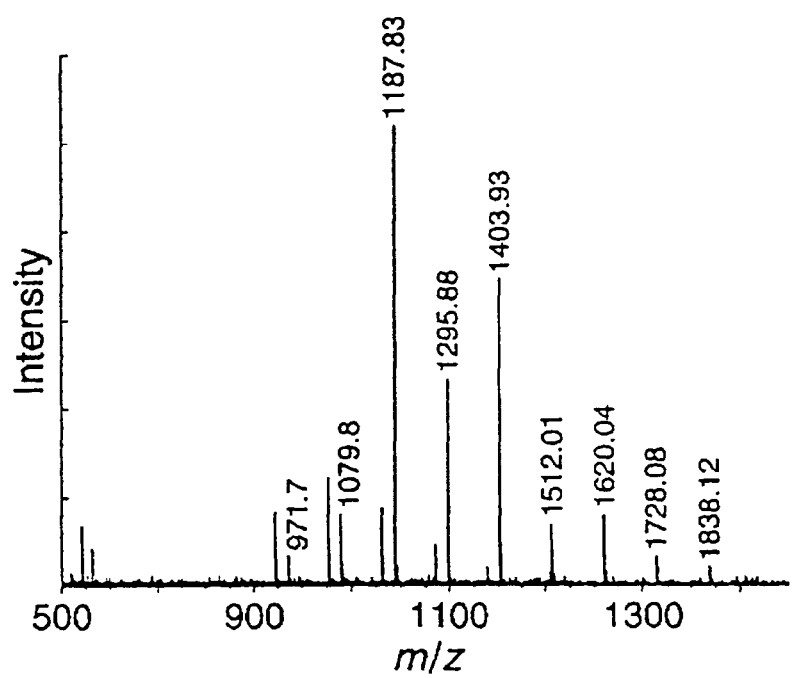
FIG. 2 shows the mass spectrum of oligo(vinylsulfonic acid) as purified from MES buffer. The molecular mass of vinylsulfonic acid ($C_2H_4O_3S$) is 108 g/mol.

Matrix-assisted laser desorption ionization mass spectrometry of the retentate containing RNase A and the inhibitor revealed a heterogeneous mixture of small molecules of a molecular mass of 900-2,000 g/mol. The inhibitor was then separated from RNase A by adding a solution of ammonium acetate (0.10 M) to the mixture. After repeatedly concentrating and adding ammonium acetate solution to the mixture, unbound inhibitor moved to the eluate, whereas RNase A remained in the retentate. Matrix-assisted laser desorption ionization mass spectrometry of the free inhibitor revealed the same heterogeneous distribution of molecular mass with individual peaks separated by 108 g/mol (FIG. 2). Because the molecular mass of vinylsulfonic acid (2) is 108 g/mol, we reasoned that the inhibitor was an oligomer of vinylsulfonic acid (OVS, 4).

Inhibition of RNase by OVS—Inhibition of RNase A activity was measured in 0.05 M imidazole-HCl buffer, pH 6.0, containing NaCl (0.10 M) and commercial OVS (Mw ~2,000, 0-1.43 microM). OVS inhibition of RNase A is not time-dependent (data not shown). The addition of NaCl diminishes the OVS inhibition of RNase A, indicating that OVS is a reversible inhibitor of the enzyme. OVS inhibits RNase A at concentrations well below that of substrate; thus, inhibition by OVS is not attributable simply to its sequestering of RNA.

Double-reciprocal plots of RNase A catalytic activity versus the concentration of poly(C) at different OVS concentrations reveal that OVS inhibits RNase A in a competitive manner (FIG. 3). With poly(C) as a substrate, the apparent Ki (0.40±0.03) microM at 0.10 M NaCl. A replot of (Km/Vmax) app versus [OVS] reveals a straight line, which is indicative of simple competitive inhibition (Cleland, 1977).

Salt Dependence of Inhibition by OVS—The Ki of OVS was measured at four different salt concentrations in 50 mM imidazole-HCl buffer, pH 6.0. Because OVS inhibits RNase A in a competitive manner, a sensitive fluorescent assay to assess inhibition by OVS. OVS inhibition of RNase A is highly salt-dependent (FIG. 4A). At 0 M NaCl, OVS inhibits catalysis by RNase A with a low inhibition constant of Ki= (11±2) pM. At 0M NaCl, the inhibition curve was fitted to a tight-binding inhibitor equation, yet the curve still exhibits some cooperativity. At 0.10 M NaCl, OVS inhibits RNase A with an inhibition constant of Ki=(120±10) nM. According to polyelectrolyte theory, the slope of a plot of log(Ki) versus log([cation]) reveals the number of Coulombic interactions between a ligand and a polyanion (28). OVS makes on average 7.8 ionic interactions with RNase A (FIG. 4B).

RNase A Inhibition by OVS Analogs—To assess the importance of the sulfonic acid group for RNase A inhibition, poly(vinylphosphoric acid) (PVP) and poly(vinylsulfuric acid) (PVOS) were tested for inhibition of ribonucleolytic activity in the fluorescent assay in the examples herein. These analogs are also good inhibitors of RNase A but are slightly less effective than is OVS (Table I). The average molecular masses of PVP and PVOS were 20,000 and 170,000 g/mol, respectively.

Oligomers of commercial OVS (with Mw~2,000 g/mol) could tightly bind to two RNase A molecules. Assuming similar binding configuration, the PVP and PVOS polymers assessed could tightly bind to more RNase A molecules. To allow a more direct comparison of inhibition by OVS, PVP, and PVOS, the data listed in Table I are in units of mass rather than moles. Poly(vinylsulfuric acid) exhibits a similar salt dependence to that observed for OVS (data not shown).

Synthesis of Solid-Bound Polymers of Vinylsulfonic Acid—Chemicals and solvents were obtained from Aldrich (St Louis Mo.). Amine-derivatized silica gel was obtained from Silicycle (Quebec City, Quebec). The derivatized silica gel employed had loading of 1.6 mmol/g (9% carbon), particle size 40-63 micron, pore size 60 and specific surface area of 500 m²/g. Anhydrous THF, DMF, and CH₂Cl₂ were obtained from a CYCLE-TAINER® solvent delivery system (Baker). Other anhydrous solvents were obtained in septum-sealed bottles.

Synthesis of acrylamide-functionalized silica gel—Acrylamide-functionalized silica gel was functionalized as indicated:

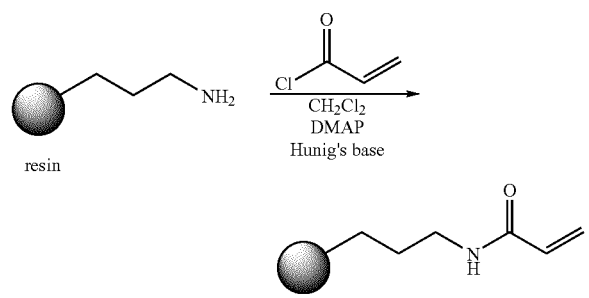

Silica gel (i.e., resin) that had been functionalized with 3-aminopropyltriethoxysilane (5.0 g, 7.3 mmol; Silicycle (Québec City, Canada), product # R52030B) was suspended in dichloromethane (50 mL). To this suspension was added dimethylaminopyridine (DMAP; 0.9 g, 7.3 mmol). The resulting suspension was flushed with Ar(g), and then cooled to 0° C. Acroyl chloride (2.6 g, 29.2 mmol, see above equation) was then added dropwise, followed by the dropwise addition of diisopropylethylamine (Hunig's base; 7.55 g, 58.4 mmol). The resulting reaction mixture was allowed to warm to room temperature, and then stirred for 12 h under Ar(g). The functionalized resin was filtered and washed sequentially with dichloromethane (5×100 mL), dimethylformamide (5×100 mL), water (5×100 mL), and diethylether (5×100 mL). The resin was then dried under reduced pressure for 12 h, and stored at 4° C.

Synthesis of Polyvinylsulfonic Acid-Functionalized Silica Gel—Solid-bound polymers of vinyl sulfonic acid were prepared as follows:

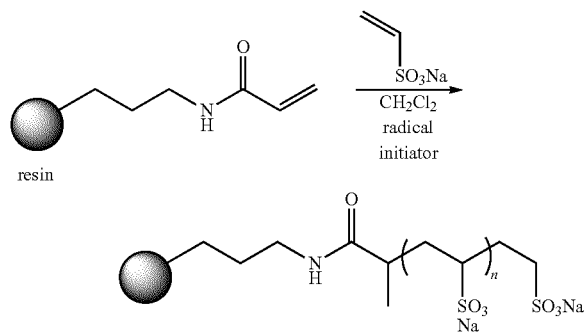

Silica gel functionalized with acrylamide (1.0 g, 1.35 mmol) was suspended in degassed H₂O (30 mL). The resulting suspension was flushed with Ar(g) and sodium vinylsulfonate (17.5 g, 135 mmol, purified to remove MEHQ inhibitor and dried to a white paste) was added. The radical initiator 2,2'-azobis(2-methylpropionamideine) dihydrochloride (42 mg, 0.15 mmol) was then added. The reaction mixture was heated to 70° C. and allowed to stir 48 h under Ar(g). The resin was filtered and washed sequentially with dichloromethane (CH₂Cl₂, 5×100 mL), dimethylformamide (DMF, 5×100 mL), water (5×100 mL), and diethylether (Et₂O, 5×100 mL). The resulting resin was dried under reduced pressure for 12 h and stored at 4° C.

Binding of RNase A to Silica gel-Immobilized PVS—RNase A (1-128 μM) was incubated with PVS-coated silica (0.1 mg) for 2 h at room temperature in 0.10 mL of 50 mM MES-NaOH buffer, pH 6.0, containing NaCl (0.10 M). The resin was collected by centrifugation at 5000 g for 10 s. The supernatant was tested for ribonucleolytic activity with a sensitive assay based on a fluorogenic substrate: 6-FAM-dArUdAdA-6-TAMRA. (Kelemen, B. R.; Klink, T. A.; Behlke, M. A.; Eubanks, S. R.; Leland, P. A.; Raines, R. T. Nucleic Acids Res. 1999, 27, 3696-3701). The concentrations of free and bound RNase A were determined and subjected to Scatchard analysis. Assays were performed in triplicate. The resulting Scatchard plot of the data is curvilinear (FIG. 6A), as expected for binding of a ligand to a lattice of sites (McGhee, J. D.; von Hippel, P. H. J. Mol. Biol. 1974, 86, (2), 469-489.) The equilibrium dissociation constants of the tightest binding sites were determined from the limiting slope of the Scatchard plot (Rahman, M. H.; Kang, I.; Waterbury, R. G.; Narang, U.; Bright, F. V.; Wang, J. H. Anal. Chem. 1996, 68, 134-138.) The PVS-coated silica has 4.1 μmol/g of tight-binding sites for RNase A and $K_d$=80 nM for these sites. This $K_d$ value is in agreement with the inhibition constant observed using free PVS ($K_i$=120 nM) (Smith et al. (2003) supra). In the presence of PVS-coated silica with excess tight-binding sites, residual ribonucleolytic activity is not detectable (<0.01%).

Figure 6B:
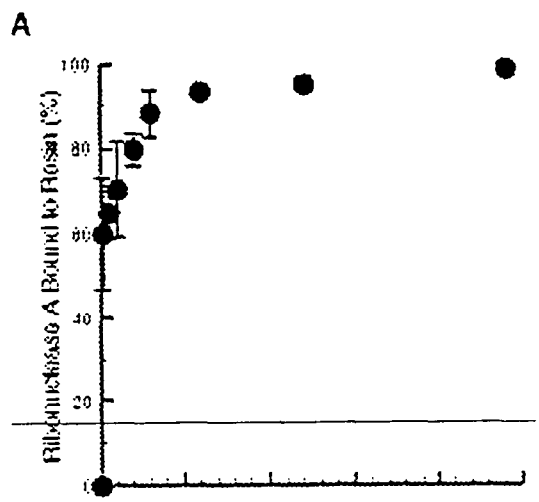

Immobilized PVS prepared as described above (0.1 mg) was incubated with RNase A (2:M) in 0.1 mL of 0.05 M MES-NaOH buffer (pH 6.0) containing NaCl (0.10M) at 25EC. The resin was collected by gentle centrifugation (5000 g for 10 sec.) at selected times, and an aliquot of supernatant was tested for ribonucleotytic activity. The resin removed substantially all detectable RNase A from the solution within about 1 hour. The results are shown in FIG. 6B. In these experiments the number of tight-binding sights was only twofold greater than the amount of RNase. Half of the RNase was bound within 1 min.; maximum binding occurred within 1 hr.

Figure 6C:
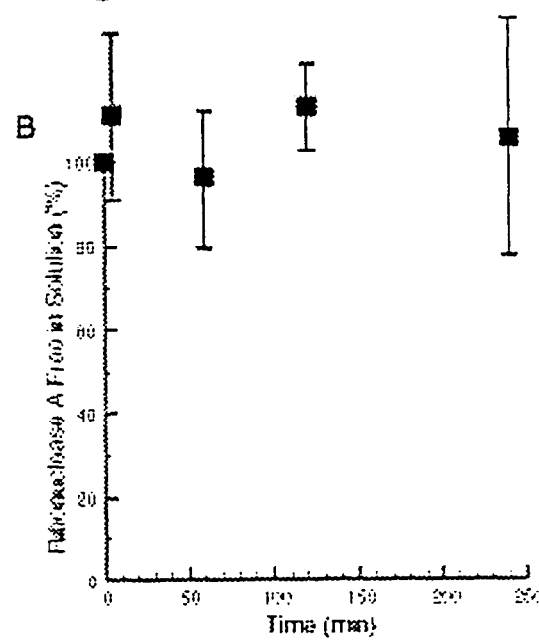

As a control, acrylamide resin (0.1 mg) was incubated with RNase A (2:M) in in 0.1 mL of 0.05 M MES-NaOH buffer (pH 6.0) containing NaCl (0.10M) at 25° C. The control resin was collected by gentle centrifugation at selected times, and an aliquot of supernatant was tested for ribonucleotytic activity. The control resin did not remove a significant amount of RNase A from the solution. The results are shown in FIG. 6C.

Figure 7:
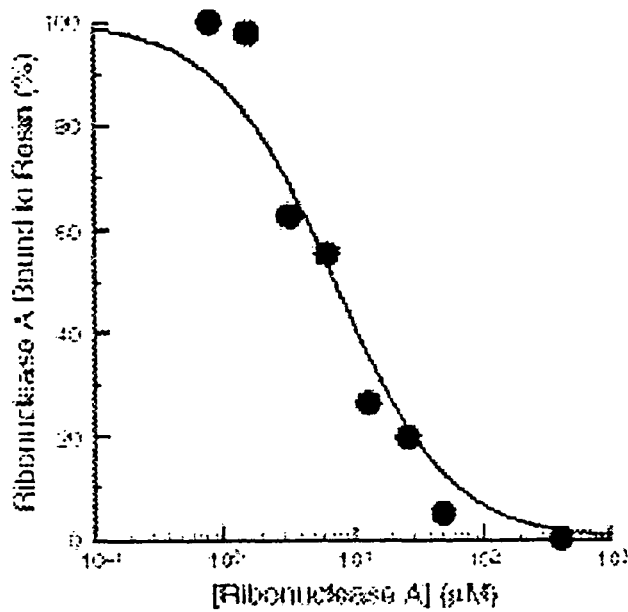
FIG. 7 is a graph of the titration of immobilized PVS with RNase.

Immobilized PVS (0.1 mg) (silica gel immobilization described above) was mixed with varying amounts of RNase A in 0.1 mL of 0.05 M MES-NaOH buffer (pH 6.0) containing NaCl (0.10M) at 25° C. After 2 h, the resin was collected by gentle centrifugation, and the supernatant was tested for ribonucleolytic activity. From these data, the capacity of the immobilized PVS for RNase A was determined to be 3.5× $10^{-6}$ mol (=5×$10^{-2}$ g) of RNase A per gram of immobilized PVS. The results are presented in FIG. 7.

Figure 8:
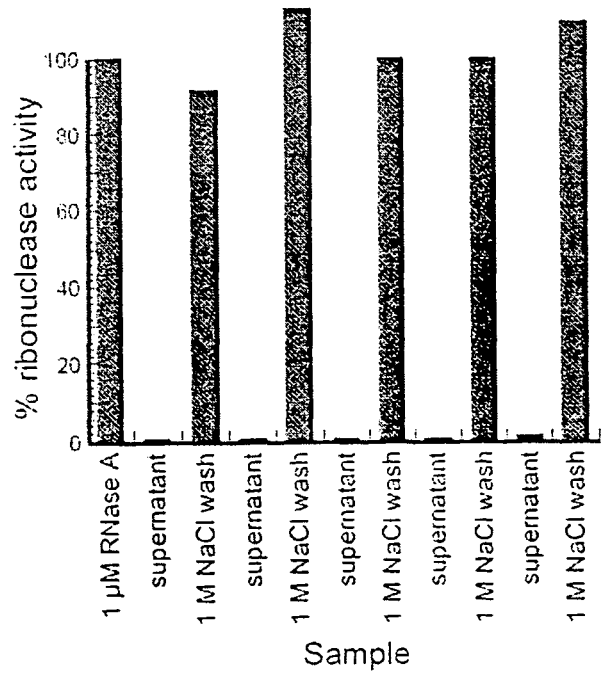
FIG. 8 is a graph illustrating adsorption of a ribonuclease during repeated use of a poly(vinylsulfonate)-coated surface. PVS-coated silica (10 mg) was mixed at room temperature for 2 h with RNase A (1.0 μM) in 1.0 mL of 50 mM MES-NaOH buffer, pH 6.0, containing NaCl (0.10 M). The silica was collected by centrifugation. The supernatant was removed, and an aliquot was assayed for ribonucleolytic activity. The resin was then washed with 1.0 M NaCl and collected by centrifugation. The supernatant was again assayed for ribonucleolytic activity. The resin was then washed thoroughly with $H_2O$. A new aliquot of RNase A was added, and the process was repeated five times.

Adsorption of Contaminating Human Ribonucleases by PVS-Coated Silica—MES-NaOH buffer (0.05 M), pH 6.0, containing NaCl (0.10 M) was contaminated with nucleases by swiping a human finger on the inside of the tube. The buffer was passed through a 0.2-μm sterile filter to remove any human or microbial cells. One mL of nuclease-contaminated buffer was mixed with PVS-coated resin (10 mg), acrylamide-coated resin (10 mg), or no resin for 2 h at room temperature. The resin was collected by centrifugation at 5,000 g for 10 s. The supernatant was removed and assayed for ribonucleolytic activity as follows. Each sample was incubated with 16S and 23S rRNA (4 μg; Roche) overnight at 37° C. As controls, a sample of non-contaminated buffer and a sample of RNase A (10 pM) were incubated likewise. An aliquot (10 μL) of each sample was then mixed with loading dye and subjected to electrophoresis for 15 min at 100 V through a 1.0% (w/v) agarose gel in TAE buffer (40 mM Tris-acetic acid, 1 mM EDTA) containing ethidium bromide (6 μg/mL). Results are shown in FIG. 8. PVS-coated silica prevents RNA degradation buffer contaminated intentionally with nucleases from human skin. Under conditions similar to those used for RNase A, a solution of human RNase 1 is >99.5% bound by PVS-coated silica.

Figure 9:
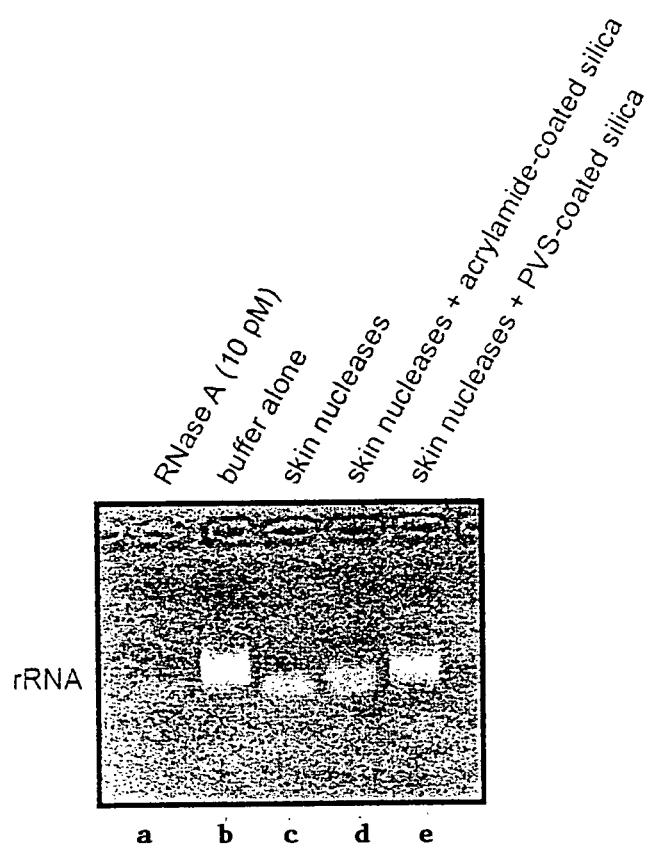
FIG. 9 is a photograph of agarose gel electrophoresis which illustrates adsorption of human skin ribonucleases by a poly(vinylsulfonate)-coated surface to protect r-RNA in samples. Buffer was intentionally contaminated with human ribonucleases (columns c-e). PVS-coated silica sequestered added ribonucleases and protected the integrity of rRNA in the sample of column e.

Reuse of PVS-Coated Silica—PVS-coated silica (10 mg) was mixed at room temperature for 2 h with RNase A (1.0 μM) in 1.0 mL of 0.05 M MES-NaOH buffer, pH 6.0, containing NaCl (0.10 M). The resin was collected by centrifugation at 5,000 g for 10 s. The supernatant was removed, and an aliquot was assayed for ribonucleolytic activity. The resin was then washed with 1.0 M NaCl (2×1.0 mL). The resin was again collected by centrifugation, and the supernatant was assayed for ribonucleolytic activity. The resin was then washed thoroughly with water. A new aliquot of RNase A was then added, and the entire process was repeated five times. This incubation/elution cycle was repeated five times with no detectable change in the amount of RNase sequestered or released (see FIG. 9).

Synthesis of Acrylamide-Coated Glass—A glass slide (75×25 mm) functionalized with 3-aminopropyltriethoxysilane was placed in $CH_2Cl_2$ (50 mL). Dimethylaminopyridine (0.9 g, 7.3 mmol) was then added. The slide was flushed with Ar(g) and cooled to 0° C. Acrolyl chloride (2.6 g, 29.2 mmol) was added dropwise, followed by the dropwise addition of diisopropylethylamine (7.55 g, 58.4 mmol). The reaction mixture was allowed to warm to room temperature, and then stirred for 12 h under Ar(g). The slide was washed with $CH_2Cl_2$ (5×100 mL), DMF (5×100 mL), water (5×100 mL), and $Et_2O$ (5×100 mL). The slide was then dried under reduced pressure for 12 h and stored at 4° C.

Synthesis of PVS-Coated Glass—An acrylamide-coated glass slide (75×25 mm) was placed in degassed water (30 mL), which was then flushed with Ar(g). Sodium vinylsulfonate (17.5 g, 135 mmol, purified to remove MEHQ and dried to a white paste) was added, followed by 2,2'-azobis(2-methylpropionamideine)-dihydrochloride (42 mg, 0.15 mmol). The reaction mixture was heated to 70° C., and then allowed to stir for 48 h under Ar(g). The slide was washed with $CH_2Cl_2$ (5×100 mL), DMF (5×100 mL), water (5×100 mL), and $Et_2O$ (5×100 mL). The slide was then dried under reduced pressure for 12 h and stored at 4° C.

REFERENCES

1. Wolfenden, R., and Snider, M. J. (2001) Acc. Chem. Res. 34, 938-945
2. Ross, J. (1996) Trends Genet. 12, 171-175
3. Raines, R. T. (1998) Chem. Rev. 98, 1045-1065
4. Russo, A., Acharya, K. R., and Shapiro, R. (2001) Methods Enzymol. 341, 629-648
5. Fontecilla-Camps, J. C., de Llorens, R., le Du, M. H., and Cuchillo, C. M. (1994) J. Biol. Chem. 269, 21526-21531
6. Lee, F. S., Shapiro, R., and Vallee, B. L. (1989) Biochemistry 28, 225-230
7. Kobe, B., and Deisenhofer, J. (1996) J. Mol. Biol. 264, 1028-1043
8. Russo, N., and Shapiro, R. (1999) J. Biol. Chem. 274, 14902-14908
9. Kim, B.-M., Schultz, L. W., and Raines, R. T. (1999) Protein Sci. 8, 430-434
10. Park, C., and Raines, R. T. (2000) FEBS Lett. 468, 199-202
11. delCardayré, S. B., Ribó, M., Yokel, E. M., Quirk, D. J., Rutter, W. J., and Raines, R. T. (1995) Protein Eng. 8, 261-273
12. Kim, J.-S., and Raines, R. T. (1993) J. Biol. Chem. 268, 17392-17396
13. Sela, M., Anfinsen, C. B., and Harrington, W. F. (1957) Biochim. Biophys. Acta 26, 502-512
14. Yakovlev, G. I., Moiseyev, G. P., Bezborodova, S. I., Both, V., and Sevcik, J. (1992) Eur. J. Biochem. 204, 187-190
15. delCardayré, S. B., and Raines, R. T. (1994) Biochemistry 33, 6031-6037
16. Kelemen, B. R., Klink, T. A., Behlke, M. A., Eubanks, S. R., Leland, P. A., and Raines, R. T. (1999) Nucleic Acids Res. 27, 3696-3701
17. Park, C., Kelemen, B. R., Klink, T. A., Sweeney, R. Y., Behlke, M. A., Eubanks, S. R., and Raines, R. T. (2001) Methods Enzymol. 341, 81-94
18. Henderson, P. J. F. (1972) Biochem. J. 127, 321-333
19. Good, N. E., Winget, G. D., Winter, W., Connolly, T. N., Izawa, S., and Singh, R. M. (1966) Biochemistry 5, 467-477
20. Ui, N. (1971) Biochim. Biophys. Acta 229, 567-581
21. Ciglic, M. I., Jackson, P. J., Raillard, S. A., Haugg, M., Jermann, T. M., Opitz, J. G., Trabesinger-Ruf, N., and Benner, S. A. (1998) Biochemistry 37, 4008-4022
22. Stowell, J. K., Widlanski, T. S., Kuteladze, T. G., and Raines, R. T. (1995) J. Org. Chem. 60, 6930-6936
23. Breslow, D. S., and Hulse, G. E. (1954) J. Am. Chem. Soc. 76, 6399-6401
24. Cleland, W. W. (1977) Adv. Enzymol. Relat. Areas Mol. Biol. 45, 273-387
25. Nelson, C. A., and Hummel, J. P. (1961) J. Biol. Chem. 236, 3173-3176
26. Sela, M. (1962) J. Biol. Chem. 237, 418-421
27. Richards, F. M., and Wyckoff, H. W. (1971) in The Enzymes (Boyer, P. D., ed) Vol. IV, 3rd Ed., pp. 647-806, Academic Press, New York
28. Record, M. T., Jr., Lohman, T. M., and de Haseth, P. (1976) J. Mol. Biol. 107, 145-158
29. Niehaus, W. G., and Flynn, T. (1993) Mycopathologia 123, 155-158
30. Niehaus, W. G., White, R. H., Richardson, S. B., Bourne, A., and Ray, W. K. (1995) Arch. Biochem. Biophys. 324, 325-330
31. Zöllner, N., and Fellig, J. (1953) Am. J. Physiol. 173, 223-228
32. Heymann, H., Gulick, Z. R., Boer, C. J. D., de Stevens, G., and Mayer, R. L. (1958) Arch. Biochem. Biophys. 73, 366-383
33. Fellig, J., and Wiley, C. E. (1959) Arch. Biochem. Biophys. 85, 313-316
34. Littauer, U. Z., and Sela, M. (1962) Biochim. Biophys. Acta 61, 609-611
35. Bach, M. K. (1964) Biochim. Biophys. Acta 91, 619-626
36. Cheng, T., Polmar, S. K., and Kazazian, H. H., Jr. (1974) J. Biol. Chem. 249, 1781-1786

37. Mach, B., Koblet, H., and Gros, D. (1968) Proc. Natl. Acad. Sci. U.S.A. 59, 445-452
38. Chambon, P., Ramuz, M., Mandel, P., and Doly, J. (1967) Biochim. Biophys. Acta 149, 584-586
39. Althaus, I. W., LeMay, R. J., Gonzales, A. J., Deibel, M. R., Sharma, S. K., Kezdy, F. J., Resnick, L., Busso, M. E., Aristoff, P. A., and Reusser, F. (1992) Experientia 48, 1127-1132
40. del Rosario, E. J., and Hammes, G. G. (1969) Biochemistry 8, 1884-1889
41. Edelhoch, H., and Coleman, J. (1956) J. Biol. Chem. 219, 351-363
42. Irie, M. (1965) J. Biochem. (Tokyo) 57, 355-362
43. Libonati, M., and Sorrentino, S. (1992) Mol. Cell. Biochem. 117, 139-151
44. Park, C., and Raines, R. T. (2001) J. Am. Chem. Soc. 123, 11472-11479
45. Park, C., and Raines, R. T. (2003) Biochemistry 42, 3509-3518
46. Fisher, B. M., Grilley, J. E., and Raines, R. T. (1998) J. Biol. Chem. 273, 34134-34138
47. Smith, B. D. and Raines, R. T. (2003), J. Biol. Chem. 278(23):20934-20938 (published JBC Papers in Press Mar. 20, 2003).
48. Bientema, J. J., 1987 Life Chemistry Reports, 4:333-389.
49. R. Kisilevsky et al. (2002) Antimicrob. Agents Chemother. 46(8) 2619-2626.
50. Linquist, R. N. et al. (1973) J. Amer. Chem. Soc. 95:8762-8768.
51. Wlodawer, A. et al. (1983) Proc. Natl. Acad. Sci. USA 80:3628-3631.
52. Berger, S. L. and Birkenmeier, C. S. (1979) Biochemistry 18:5145.
53. Jocoli and Ronald (1973) Can. J. Biochem, 51:1558-1565.
54. Jones (1976) Biochem Biophys Res. Commun, 69:469-474.
55. Mendelsohn and Young Biochem. Biophys. Acta (1978) 519:461-473.
56. Allewell and Sama (1974) Biochem. Biophys. Acta, 341-484-488.
57. Dailer and Kerber (1955) Makromol. Chem. 17:56.
58. L. H. Sperling, Introduction to Physical Polymer Science, $2^{nd}$ Ed., Wiley New York (1992).
59. L. H. Sperling (1999) ACS Division of Polymeric Materials: Science and Engineering (PMSE) 81: 569.)
60. Creel, H., (1993) *Trends in Polymer Science*, "Prospects for the Analysis of High Molar Mass Polymers Using MALDI Mass Spectrometry," Elsevier, vol. 1,(11): 336-342
61. Kisilevsky et al. (1995) Nature Medicine 1(2):143-148
62. C. E. Schildknect "Vinyl and Related Polymers" (John Wiley and Sons, Inc., N.Y.) 1952, pp. 643-648

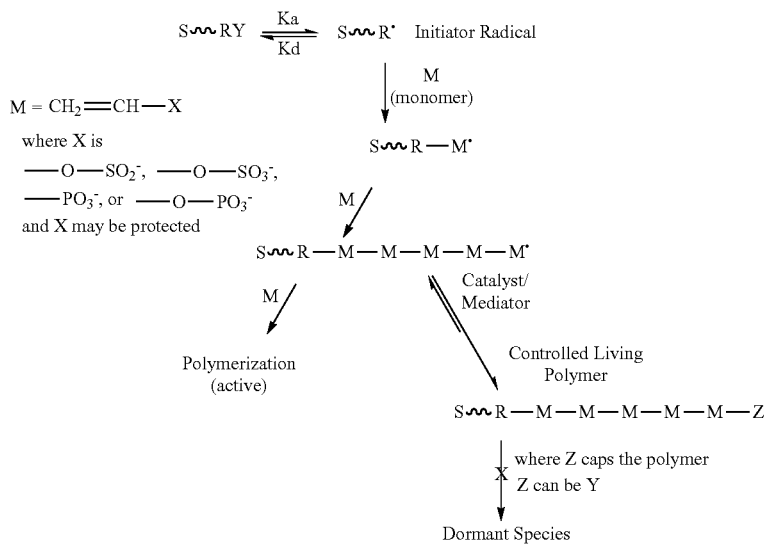

SCHEME 1

The invention claimed is:

1. A method for inhibiting one or more nuclease in vitro which comprises the step of contacting the one or more nuclease with an inhibitory composition which comprises one or more of the oligomers, polymers or both of formula:

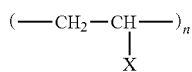

where X is $-SO_3$, $-OSO_3$ $-PO_3H$, or $-OPO_3H$, or salts thereof, n is an integer representing the number of repeating monomer units and n is 8 to 19, wherein the one or more oligomers, polymers or both are covalently bound to a solid.

2. The method of claim 1 in a biological medium wherein the contacting step comprises the step of adding the inhibitory composition to the biological medium.

3. The method of claim 1 wherein X is $-SO_3^-$.

4. The method of claim 3 wherein n is 8 to 18.

5. The method of claim 3 wherein n is 9 to 17.

6. The method of claim 1 wherein X is $-SO_3^-$.

7. The method of claim 6 wherein n is 8 to 18.

8. The method of claim 6 wherein n is 9 to 17.

9. The method of claim 1 wherein the nuclease is an RNase.

10. The method of claim 1 which comprises the step of contacting the biological medium with a material of formula:

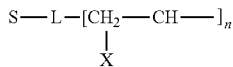

where X is —SO$_3$, —OSO$_3$—PO$_3$H, or —OPO$_3$H, or salts thereof, where n is 8 to 19, L is a linker or spacer group and S is a solid.

11. The method of claim 10 wherein X is —SO$_3^-$.

12. The method of claim 10 wherein the solid is silica gel.

13. The method of claim 10 wherein the solid is a glass surface.

14. The method of claim 10 wherein the linker is —(CH$_2$)p-NH—CO—C(CH$_3$)— where p is 1 or more.

15. The method of claim 14 wherein p is 3-10.

16. The method of claim 14 where p is greater than 10.

17. The method of claim 1 wherein the solid is silica gel particles, glass beads, glass surfaces, cross-linked polystyrene, cross-linked PEG, microspheres, plastic surfaces or plastic beads.

18. The method of claim 1 wherein the solid is the internal surface of a container in which a buffer or reagent is to be carried or stored or in which a procedure, purification, isolation, assay or reaction is to be carried out.

19. The method of claim 1 wherein the inhibitory composition is a mixture of one or more oligomers covalently bound to the solid.

20. The method of claim 10 wherein the solid is silica gel particles, glass beads, glass surfaces, cross-linked polystyrene, cross-linked PEG, microspheres, plastic surfaces or plastic beads.

21. The method of claim 10 wherein n is 8 to 18.

22. The method of claim 1 wherein n is 8 to 18.

23. The method of claim 10 wherein n is 9 to 17.

24. The method of claim 1 wherein the oligomer or polymer is covalently bonded to the solid by polymerization of monomers of the oligomer or polymer on the surface.

25. The method of claim 10 wherein the oligomer or polymer is covalently bonded to the solid by polymerization of monomers of the oligomer or polymer on linker L.

26. The method of claim 11 wherein n is 8 to 18.

27. The method of claim 10 wherein the nuclease is a RNase.

28. A method for inhibiting one or more nuclease in vitro which comprises the step of contacting the one or more nuclease with an inhibitory composition which comprises one or more of the oligomers, polymers or both of formula:

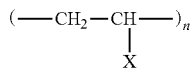

where X is —SO$_3$, —OSO$_3$—PO$_3$H, or —OPO$_3$H, or salts thereof, n is an integer representing the number of repeating monomer units and n is 8 to 19.

29. The method of claim 28 wherein n is 8 to 18.

30. The method of claim 28 wherein X is —SO$_3^-$.

31. The method of claim 30 wherein n is 8 to 18.

32. The method of claim 30 wherein n is 9-17.

33. The method of claim 1 where n is 9 to 17.

* * * * *